(12) United States Patent
Khaw et al.

(10) Patent No.: US 9,186,414 B2
(45) Date of Patent: Nov. 17, 2015

(54) COMPOSITION FOR INTRAOCULAR IMPLANTATION OF BEVACIZUMAB

(75) Inventors: Peng T. Khaw, London (GB); Stephen Brocchini, London (GB); Ashkan Khalili, Addison, IL (US)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 13/878,375

(22) PCT Filed: Oct. 7, 2011

(86) PCT No.: PCT/GB2011/001458
§ 371 (c)(1),
(2), (4) Date: Jun. 14, 2013

(87) PCT Pub. No.: WO2012/046009
PCT Pub. Date: Apr. 12, 2012

(65) Prior Publication Data
US 2013/0266630 A1    Oct. 10, 2013

(30) Foreign Application Priority Data
Oct. 8, 2010 (GB) .................................. 1017048.8

(51) Int. Cl.
*A61K 47/36* (2006.01)
*A61K 47/42* (2006.01)
*A61K 9/00* (2006.01)
*A61K 9/20* (2006.01)
*A61K 47/26* (2006.01)

(52) U.S. Cl.
CPC ............... *A61K 47/42* (2013.01); *A61K 9/0051* (2013.01); *A61K 9/205* (2013.01); *A61K 9/2095* (2013.01); *A61K 47/26* (2013.01); *A61K 47/36* (2013.01)

(58) Field of Classification Search
None
See application file for complete search history.

(56) References Cited

U.S. PATENT DOCUMENTS 7,491,391 B2 * 2/2009 Benson et al. ............. 424/139.1
2010/0098772 A1 * 4/2010 Robinson et al. ............. 424/501

FOREIGN PATENT DOCUMENTS

| WO | 2009063222 A2 | 5/2009 | |
|---|---|---|---|
| WO | WO 2009/063222 A2 * | 5/2009 | ........... A61K 31/404 |
| WO | 2010048086 A1 | 4/2010 | |

OTHER PUBLICATIONS

Kerr, Sarah J. "Teleangiectasia" (2011) Downloaded from http://medicine.med.nyu.edu/conditions-we-treat/conditions/telangiectasia on Oct. 2, 2014, 3 pages.*
Caillard et al., "Design and evaluation of succinylated soy protein tablets as delayed drug delivery systems," Int J Biol Macromol, 2009, vol. 45, pp. 414-420.
Izutsu et al., "Stabilization of protein structure in freeze-dried amorphous organic acid buffer salts," Chem Pharm Bull, 2009, vol. 57, pp. 1231-1236.
Anhorn et al., "Freeze drying of human serum albumin (HSA) nanoparticles with different excipients," Int J Pharm, 2008, vol. 363, pp. 162-169.
Schule et al., "Stabilization of IgG1 in spray-dried powders for inhalation," Eur J Pharm Biopharm, 2008, vol. 69, pp. 793-807.
Van Beek et al., "Hyaluronic acid containing hydrogels for the reduction of protein adsorption," Biomaterials, 2008, vol. 29, pp. 780-789.
Zhang et al., "Trehalose and hyaluronic acid coordinately stabilized freeze-dried pancreatic kininogenase," Eur J Pharm Biopharm, 2007, vol. 65, pp. 18-25.
Terryn et al., "Chemical Analysis of Solid-Stage Irradiated Human Insulin," Pharm Res, 2006, vol. 23, pp. 2141-2148.
Chang et al., "Effect of sorbitol and residual moisture on the stability of lyophilized antibodies: Implications for the mechanism of protein stabilization in the solid state," J Pharm Sci, vol. 94, pp. 1445-1455.
Sarciaux et al., "Effects of buffer composition and processing conditions on aggregation of bovine IgG during freeze-drying," J Pharm Sci, 1999, vol. 88, pp. 1354-1361.
ISA/EPO, International Search Report issued in related international application No. PCT/GB2011/001458, mailed Dec. 23, 2011.

* cited by examiner

*Primary Examiner* — Marcela M Cordero Garcia
*Assistant Examiner* — Mindy Newman
(74) *Attorney, Agent, or Firm* — Stites & Harbison, PLLC; Terry L. Wright

(57) ABSTRACT

A solid, compressed pharmaceutical composition comprises i) a peptide active pharmaceutical ingredient, ii) a polysaccharide excipient and/or an albumin, and iii) an oligosaccharide excipient. The polysaccharide excipient may be hyaluronic acid, or the potassium salt thereof, and the oligosaccharide excipient may be trehalose.

26 Claims, 25 Drawing Sheets

Released bevacizumab (%)

Time (hours)

COMPOSITION FOR INTRAOCULAR IMPLANTATION OF BEVACIZUMAB

The present invention relates to compositions. In particular, though not exclusively, the present invention relates to pharmaceutical compositions containing polypeptide therapeutic agents.

Therapeutic agents comprising polypeptides frequently present problems in terms of formulation and delivery to their site of action. Owing to their chemical and physical instability, and their low bioavailability, polypeptides are typically administered by injection. As a result, they are commonly formulated as aqueous solutions or freeze-dried solids for reconstitution for injection. When such a solution is administered parenterally (e.g. by subcutaneous injection), it generally only remains at the site of administration for a short period of time (i.e., a few minutes to a few hours) and then it distributes into the blood system. To avoid systemic side-effects it is often desirable to deliver therapeutic agents locally so that only the relevant part of the body is exposed to the agent. In principle this strategy provides a means to minimise the dose needed to provide a therapeutic effect. Additionally if localised administration can be accomplished utilising a final dosage form capable of prolonging the local release of an agent at a therapeutic dose, further benefit can accrue. If this situation can be met, it becomes possible to avoid dose dumping at the site of injection. Prolonging the local release of a therapeutic agent further allows that a therapeutic dose can be maintained over a longer period of time for improved efficacy. If provided as a solid dosage form (for example that can be placed into biological tissue), it is also important that any therapeutically active agent delivered to the body has a suitable dissolution profile enabling a therapeutically effective concentration of the active agent to be achieved for a sufficiently prolonged period of time to allow treatment.

In WO2009/063222, there is described a solid dosage form (a tablet) which consists of the monoclonal antibody, bevacizumab (obtained from the commercial product Avastin®), and hyaluronic acid. An excipient-free bevacizumab tablet is also described. Prior to preparation of the tablets, all the original excipients (trehalose dihydrate, polysorbate 20 and sodium phosphate) from the Avastin® product were removed.

In accordance with a first aspect of the present invention, there is provided a solid, compressed pharmaceutical composition comprising i) a peptide active pharmaceutical ingredient, ii) a polysaccharide excipient and/or an albumin, and iii) an oligosaccharide excipient.

The present invention is based on the surprising finding that the antibody composition described in WO2009/063222 can be significantly improved by formulating the antibody with an oligosaccharide and a polysaccharide (and/or an albumin). In WO2009/063222, the oligosaccharide, trehalose, is specifically removed from the composition prior to addition of the polysaccharide, hyaluronic acid. It has now been found that, when both these excipients are present (or, in some embodiments, with the polysaccharide replaced by or supplemented with an albumin), the antibody has improved chemical and physical stability, whilst the compressed composition still displays desirable drug release characteristics of the therapeutic form of the protein. Trehalose is known to be added to freeze-dried peptide-based pharmaceuticals since it is believed to prevent damage to the peptides during the drying process. However, it was unexpected that an oligosaccharide such as trehalose would interact with a polysaccharide excipient in order to improve the stability and release characteristics of a compressed peptide formulation. Solid, compressed dosage forms are particularly desirable in many therapeutic settings. For example, where the dosage form is to be handled during a surgical procedure (e.g. for implantation post-surgery), the use of a solid composition is more straight-forward than the use of a solution or gel composition.

The peptide active pharmaceutical ingredient may be any peptide, polypeptide or protein, or derivative thereof, which has pharmacological activity (e.g. biological receptor binding activity (whether agonistic or antagonistic), ligand binding activity, enzymatic activity, enzyme inhibitory activity or antigen binding activity). The peptide active pharmaceutical ingredient can include any endogenous or non-endogenous peptide that can be used therapeutically. Non-endogenous proteins include truncated antibody fragments and protein scaffolds that display pharmacological activity. The term 'peptide' as used herein also is intended to include, for example, peptides based on naturally occurring L-amino acids, peptides containing one or more D-amino acids, peptides containing one or more derivatised amino acids, peptides containing synthetic amino acids, derivatised peptides bearing one or more non-peptidic moieties, such as saccharide or poly(alkylene glycol) groups (e.g. glycosylated or PEGylated moieties), antibodies and fragments thereof, and fusion peptides.

In certain embodiments, the oligosaccharide excipient is a non-reducing sugar. In particular instances, the oligosaccharide excipient is a disaccharide. In preferred embodiments, the oligosaccharide excipient is trehalose.

In exemplary embodiments, a polysaccharide excipient is used as component (ii) of the composition. In particular embodiments, the polysaccharide excipient is anionic. The anionic polysaccharide may be present in the form of a potassium salt thereof. The molecular weight of the polysaccharide excipient may, in certain embodiments, be from approximately 1 to approximately 10 MDa, such as approximately 3 to approximately 6 MDa, in particular approximately 4 or 5 MDa. In certain embodiments, the polysaccharide excipient is non-sulphated. The polysaccharide excipient may be a glycosaminoglycan. A preferred polysaccharide excipient is hyaluronic acid, or a salt thereof.

In a particularly useful embodiment, the polysaccharide excipient is the potassium salt of an anionic polysaccharide, such as hyaluronic acid. It has been found that the replacement of sodium hyaluronate with the potassium salt thereof leads to even greater improvements in the stability of the composition of the invention. In particular, the tendency of peptides, such as antibodies, to aggregate in aqueous media following their release from the composition is significantly reduced. Alternatively or in addition, the compositions of the invention may contain potassium ions, e.g. a potassium salt, such as a potassium buffer salt (i.e. the potassium salt of a weak acid; for example, a phosphate salt of potassium). It has been found that the presence of potassium ions can lead to an improved stability of the peptide against aggregation.

In certain embodiments, the composition of the invention contains one or more further, pharmaceutically acceptable excipients. The further pharmaceutical excipients may include an albumin, such as human serum albumin. The albumin may be a recombinant albumin. Albumin has been found to further enhance the aggregation-inhibiting effects of the polysaccharide and oligosaccharide components of the composition of the invention. In other embodiments, the albumin may be employed instead of the polysaccharide excipient. It has been found that, surprisingly, an albumin is capable of leading to similar stability-enhancing effects as a polysaccharide excipient, such as hyaluronate. In other embodiments, the composition contains no further excipients (i.e. beyond the polysaccharide and oligosaccharide, or the albumin and oligosaccharide).

In preferred embodiments, the composition is sterile. In such embodiments, the composition may be sterilised post-manufacture (e.g. by means of gamma or beta radiation), although an aseptic manufacturing approach may typically be preferred.

In certain instances, the peptide active pharmaceutical ingredient, polysaccharide excipient (and/or albumin) and oligosaccharide excipient are freeze dried (optionally in the presence of a buffer comprising a potassium salt). In particular, two or more of, and optionally all three of, the peptide active pharmaceutical ingredient, polysaccharide excipient (and/or albumin) and oligosaccharide excipient may be freeze dried together. The freeze drying of the components of the composition together in this manner leads to a resulting lyophilisate akin to a solid dispersion. Such an approach can lead to enhanced stability and release characteristics. As mentioned above, the use of compressed solid compositions offers significant advantages in terms of handling (e.g. in surgical settings) compared to prior art compositions, which are typically in the form of solutions or gels (e.g. hyaluronate gels).

The compositions of the invention are in a compressed form. As used herein, the term 'compressed' means that the compositions have been prepared using a process including at least one step in which the solid contents of the composition (e.g. powder or lyophilisate) are subjected to a physical compression force, such that the volume of the composition is reduced and adhesion of the solid contents takes place. Such a definition includes a process in which volume reduction occurs by removal of solvent (e.g. water) from the solid contents of the composition (e.g. by lyophilisation) placed in a mold. The resulting volume-reduced compositions are preferably unit dosage forms. For example, in preferred embodiments, the composition may be in the form of a tablet, e.g. prepared using a tableting punch and die. In alternative embodiments, the composition takes the form of an injectable rod.

The peptide active pharmaceutical ingredient may optionally have a molecular weight of around 0.5 kDa to around 250 kDa, preferably 1 kDa or more to around 250 kDa.

In certain embodiments, the peptide active pharmaceutical ingredient is an antibody or an antigen-binding fragment thereof. Any antibody molecule may be used. The term "antibody molecule" encompasses polyclonal antibodies, monoclonal antibodies or antigen binding fragments thereof, such as Fv, Fab, F(ab')2 fragments and single chain Fv fragments. Preferably the antibody molecules are lyophilised antibody molecules. The target antigen of the antibody determines the therapeutic activity of the antibody. Numerous therapeutic antibodies are known to those skilled in the art.

In a particular embodiment, the antibody is bevacizumab. In another embodiment, the antibody is the Fab fragment contained in the product marketed as Lucentis®.

In certain embodiments, the compositions may contain multiple active pharmaceutical ingredients, such as multiple peptide active pharmaceutical ingredients, or one or more non-peptide active pharmaceutical ingredients in addition to the peptide active pharmaceutical ingredient. One or more of the peptide active pharmaceutical ingredients in a combination composition of this type may be an antibody, or an antigen-binding fragment thereof. The composition of the invention allows the dose and the rate of release of the multiple components (e.g. two or more antibodies) to be controlled independently of one another. Such control is not possible with conventional formulations of peptide active pharmaceutical ingredients. In embodiments, such a combination composition may be in the form of a tablet having multiple layers (optionally with a different active pharmaceutical ingredient in each layer), or a capsule containing multiple populations of tablets or pellets, optionally with each population containing a different active ingredient.

The peptide active pharmaceutical ingredient may be present in the composition in the form of a conjugate with one or more additional moieties capable of altering the pharmacokinetics and/or pharmacodynamics thereof. For example, the peptide active pharmaceutical ingredient may be conjugated with a hydrophilic moiety, such as a glycol moiety, for example polyethylene glycol (PEG; e.g. a PEG-antibody fragment conjugate), or with a biocompatible polymeric moiety, saccharide moiety or lipid moiety. In addition, the compositions of the invention may incorporate materials known in the drug delivery field for enhancing delivery of biomolecules, such as liposomes or cross-linked polymeric matrices, for example cross-linked polysaccharides (such as cross-linked hyaluronic acid). Such a polysaccharide may be the polysaccharide excipient required in compositions of the invention as defined above, or may be in addition thereto.

Preferably, the composition of the invention is suitable for implantation in vivo. The composition may, for example, be implantable ocularly, periocularly or intraocularly. For example, implantation may take place in the subconjunctival space, or elsewhere in the eye, such as in the posterior segment or cornea. As an additional example, the composition may be implantable subcutaneously. The dimensions of the composition may, for example, be as described for the dosage form of WO2009/063222.

In particular embodiments, the composition is coated. For example, the composition may be a coated tablet. The coating may comprise one or more polymeric ingredients, such as cellulose derivatives, as would be familiar to a person skilled in the preparation of compressed dosage forms. A coating provides additional versatility in terms of release rates, and also enhances the stability of the composition during storage.

In accordance with a second aspect, the present invention provides a solid, compressed pharmaceutical composition comprising a peptide active pharmaceutical ingredient, and potassium ions, e.g. a potassium salt, such as the potassium salt of an anionic polysaccharide, such as hyaluronic acid.

As described above, it has been found that, surprisingly, the potassium salt of hyaluronic acid produces significant improvements in formulations containing peptide drugs. Stability of the peptide, particularly against aggregation, can be improved in this manner. Alternative potassium salts (e.g. buffer salts) are also believed to have a stability-enhancing effect on the peptide. The composition is preferably implantable.

In certain embodiments, the composition of the second aspect may include a polysaccharide excipient, such as an anionic polysaccharide, such as hyaluronic acid. The polysaccharide may be included in the form of its potassium salt. In some embodiments, the composition of the second aspect may include an albumin. The albumin may be included in addition or alternative to the polysaccharide excipient. The advantages associated with the inclusion of an albumin are outlined above.

The compositions of the invention are preferably in unit dosage form.

In certain embodiments, the compositions of the invention may contain one or additional active pharmaceutical ingredients. The additional active pharmaceutical ingredients may be peptides or non-peptides, and may be indicated for the same condition or a different condition to the peptide active pharmaceutical ingredient.

In some embodiments, the compositions of the invention have a volume of between 0.1 mm$^3$ and 1.5 cm$^3$ (such as between 0.1 and 100 mm$^3$, or between 0.1 and 20 mm$^3$), and/or a maximum dimension of 5 mm or less, and/or a weight of 10 mg or less. Such limits allow the composition to be implanted in a wider variety of sites in vivo.

In another aspect, the present invention also provides a composition as defined in the first or second aspects, for use in therapy.

The composition of the invention may be fabricated for implantation in a wide variety of sites within the human or animal body. Ocular uses are discussed in particular detail herein, but the composition may be adapted for implantation in any cavity in which fluid is available for release of the peptide, for example peritoneal, pulmonary or intracranial implantation. Non-fluid-filled cavity implantation, such as subcutaneous delivery, may also be possible, with dissolution of the peptide occurring in the interstitial fluid. In embodiments in which the composition is in the form of an injectable rod, administration may take place by means of a needle-based or needle-free injection, thereby avoiding the need for surgical intervention to effect the implantation.

Where the peptide active pharmaceutical ingredient is an antiangiogenic agent (such as bevacizumab), the composition can be used to treat vasculoproliferative conditions in a range of sites. Such conditions may be manifest in ocular sites (e.g. macular degeneration) or in a wide range of other sites in the human or animal body. It is known to use Avastin® or Lucentis® for macular degeneration by injection of a solution of the product into the eye. However, since the active ingredient is rapidly washed out of the eye, the injections must be repeated relatively frequently. The compositions of the invention, on the other hand, allow delivery of the active ingredient by means of a single implantation, which leads to slow release of the active ingredient and obviates the need for frequent injections.

Such compositions of the invention can also be used to prevent scarring in ocular sites, and also in other implantation sites. Thus, such a composition can have a wide range of implantation sites for the prevention of scarring during wound healing in various tissues. In addition, such a composition can be implanted within or in the vicinity of a tumour, to prevent growth and/or metastasis of the tumour. Indeed, any condition for which the known Avastin® or Lucentis® products can be used, and where they exert an antiangiogenic effect. may be susceptible to intervention using the composition of the invention, provided a suitable implantation site can be used.

Thus, compositions of the invention can potentially be used for the treatment of vasculoproliferative conditions, for example conditions involving neovascularisation, vascular endothelial cell proliferation, angiogenesis, telangiectasia or microaneurysms, for the treatment of a disorder of the eye that is selected from diabetic retinopathy, retinal vein occlusion, retinopathy of prematurity, macular telangiectasia, age-related macular degeneration or choroidal neovascularisation, or for the treatment of a tumour that may be selected from brain tumour, breast tumour, kidney tumour, colorectal tumour, lung tumour, prostate tumour, head and neck tumours, stomach tumour, pancreatic tumour, skin tumour, cervical tumour, bone tumour, ovarian tumour, testicular tumour and liver tumours.

The invention also provides a composition as defined in the first or second aspects and containing a peptide active pharmaceutical ingredient which has an antiangiogenic effect, for use in the treatment or prevention of a condition selected from those mentioned above.

In a related aspect, the invention also provides a composition as defined in the first or second aspects and containing bevacizumab, for use in the treatment of neoplastic conditions, macular degeneration, diabetic retinopathy, corneal angiogenesis, or for the prevention of scarring, for example following glaucoma filtration surgery.

The invention also provides a method for the treatment of a condition selected from those mentioned above, the method comprising the administration, to a subject in need of such treatment or prevention (for example, implantation into a suitable site of such a subject), of a composition according to the first or second aspects and containing a peptide active pharmaceutical ingredient which has an antiangiogenic effect.

Similarly, the invention also provides a method for the treatment of neoplastic conditions, macular degeneration, diabetic retinopathy, or corneal angiogenesis, or for the prevention of scarring, for example following glaucoma filtration surgery, the method comprising the administration, to a subject in need of such treatment or prevention (for example, implantation into a suitable site of such a subject), of a composition according to the first or second aspects and containing an anti-VEGF antibody, such as bevacizumab.

The invention also provides the use of a composition according to the first or second aspects and containing a peptide active pharmaceutical ingredient which has an antiangiogenic effect, for the preparation of a medicament for the treatment of a condition selected from those mentioned above.

Also provided is the use of a composition according to the first or second aspects and containing an anti-VEGF antibody, such as bevacizumab, for the preparation of a medicament for the treatment of neoplastic conditions, macular degeneration, diabetic retinopathy, or corneal angiogenesis, or for the prevention of scarring, for example following glaucoma filtration surgery.

In particular embodiments, the composition is administered by ocular, periocular or intraocular implantation. The composition may be implanted in the subconjunctival space. Implantation is also possible within the cornea, and in the posterior segment.

The invention will now be described in more detail by way of example only and with reference to the appended drawings, of which:

FIG. 1 shows the results of a dissolution test performed on a bevacizumab tablet according to the invention;

FIG. 2 shows a molecular weight comparison of bevacizumab released from a tablet according to the invention and bevacizumab from the Avastin® formulation. The dark line and bar (inset) shows bevacizumab form the Avastin® formulation, while the lighter line and bar (inset, right) show that from the tissue tablet. Both samples of the antibody eluted at 76.8 minutes (UV, 280 nm) and showed a similar area under the curve (inset, top). The molecular weight comparison was also performed by gel electrophoresis (SDS-PAGE) (inset, bottom);

FIG. 3 shows a binding affinity comparison (biosensor Biacore X-100, using VEGF$_{165}$ on a CM5 chip) of bevacizumab released from a tablet according to the invention and bevacizumab from the Avastin® formulation. The slightly lower trace shows binding of the antibody from the tissue tablet, but the two traces show essentially the same overall binding response;

FIG. 4 shows an in vitro biological efficacy (inhibition of cell proliferation) comparison of bevacizumab released from a tablet according to the invention and bevacizumab from the Avastin® formulation. Formulations were prepared at different antibody concentrations relative to VEGF (media control, 2000:3 Ab:VEGF Avastin®, 2000:3 Ab:VEGF tablet, 1000:3 Ab:VEGF Avastin®, 1000:3 Ab:VEGF tablet, 100:3 Ab:VEGF Avastin®, 100:3 Ab:VEGF tablet, media+VEGF control).

FIG. 5 shows the results of an angiogenesis assay, comparing the effects on VEGF-stimulated angiogenesis of bevacizumab from Avastin® and from a tablet according to the invention. The graphs report various parameters including the number of branches that reach half of the longest and the number of branches at day 7. From the left, the bars show 10:1 bevacizumab:VEGF Avastin®, 10:1 bevacizumab:VEGF tablet of invention, 1:2 bevacizumab:VEGF Avastin®, 1:2 bevacizumab:VEGF tablet of invention; and media+VEGF control;

Figure 8:
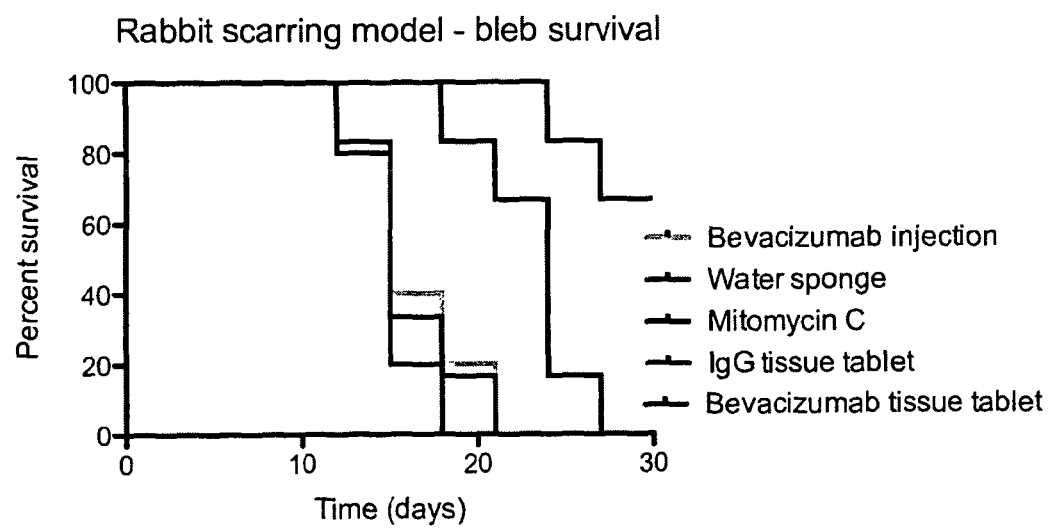
Figure 9:
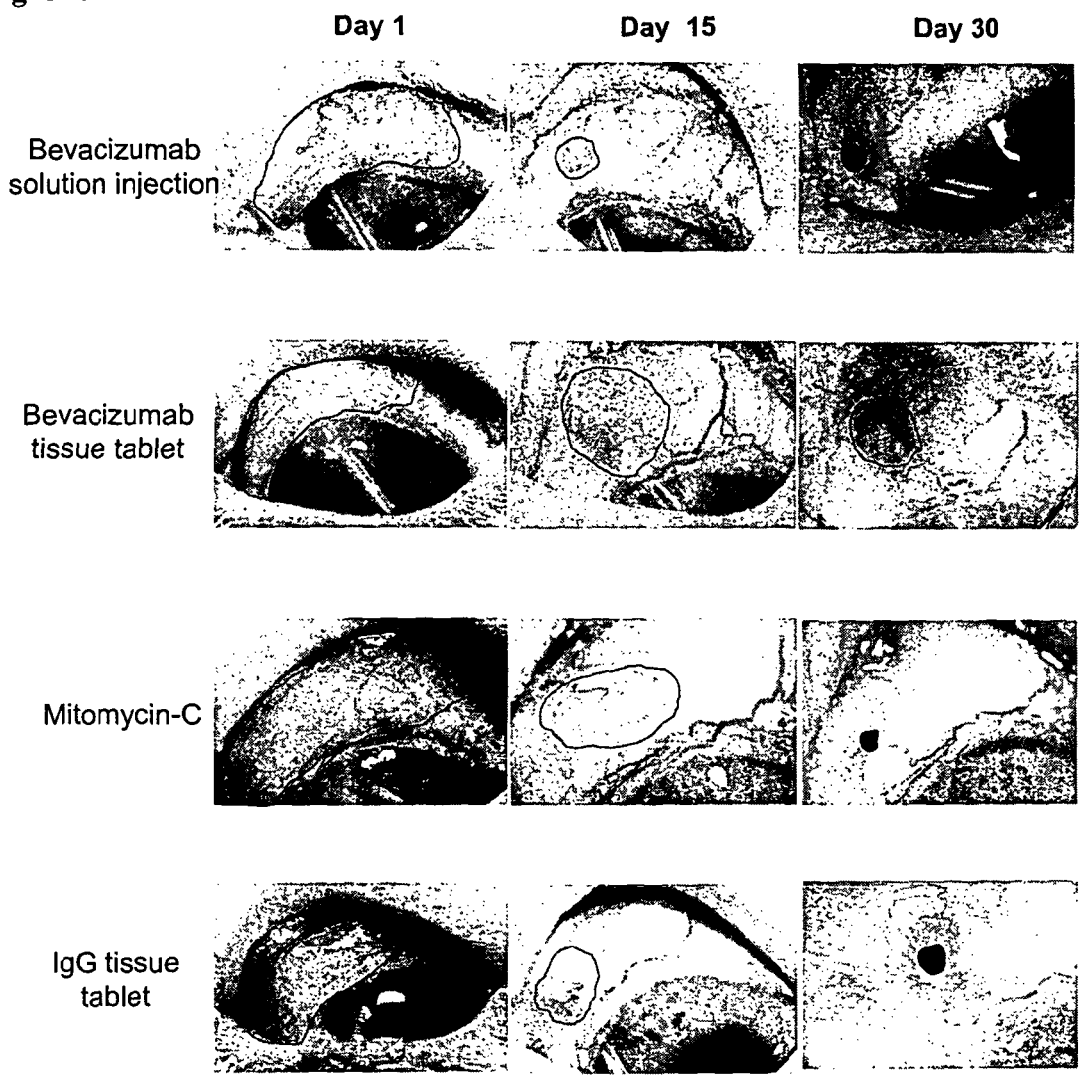
Figure 10:
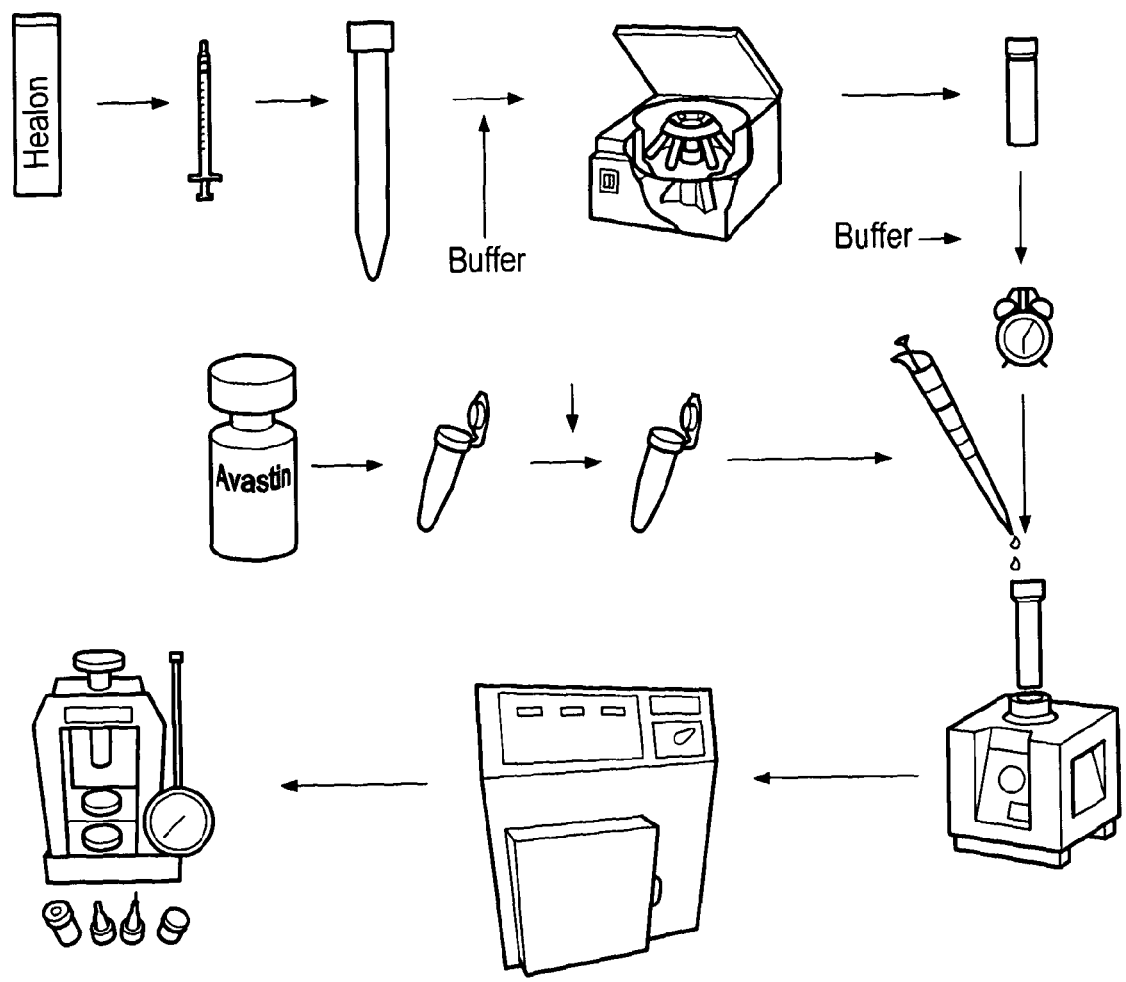
Figure 11:
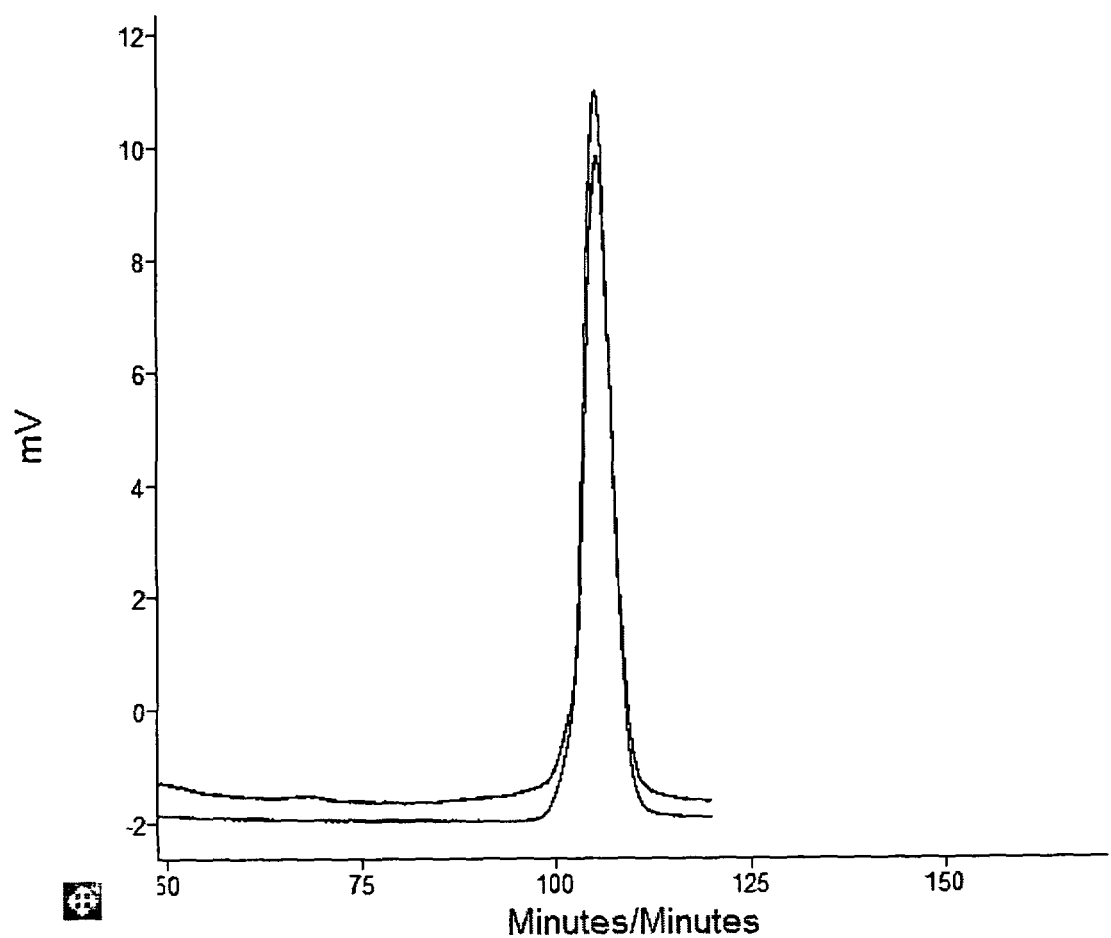
Figure 12:
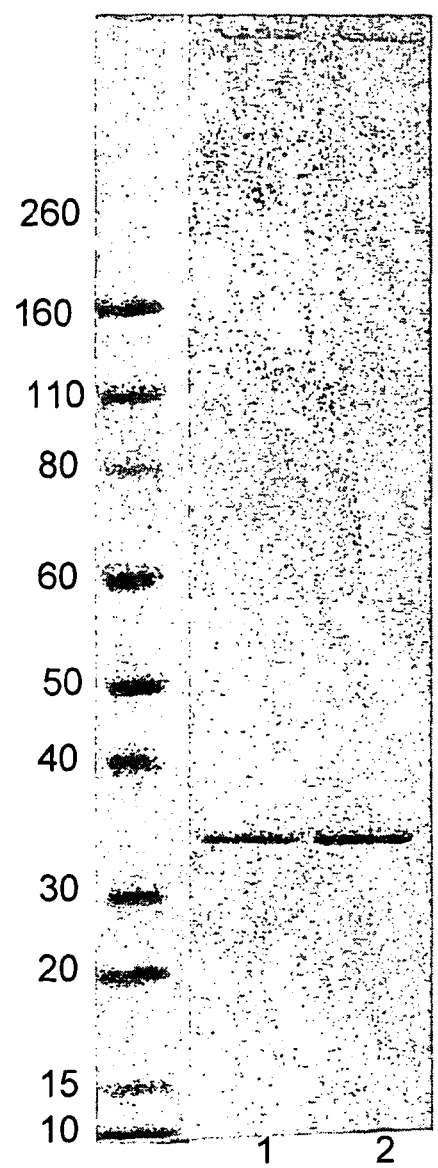
Figure 13:
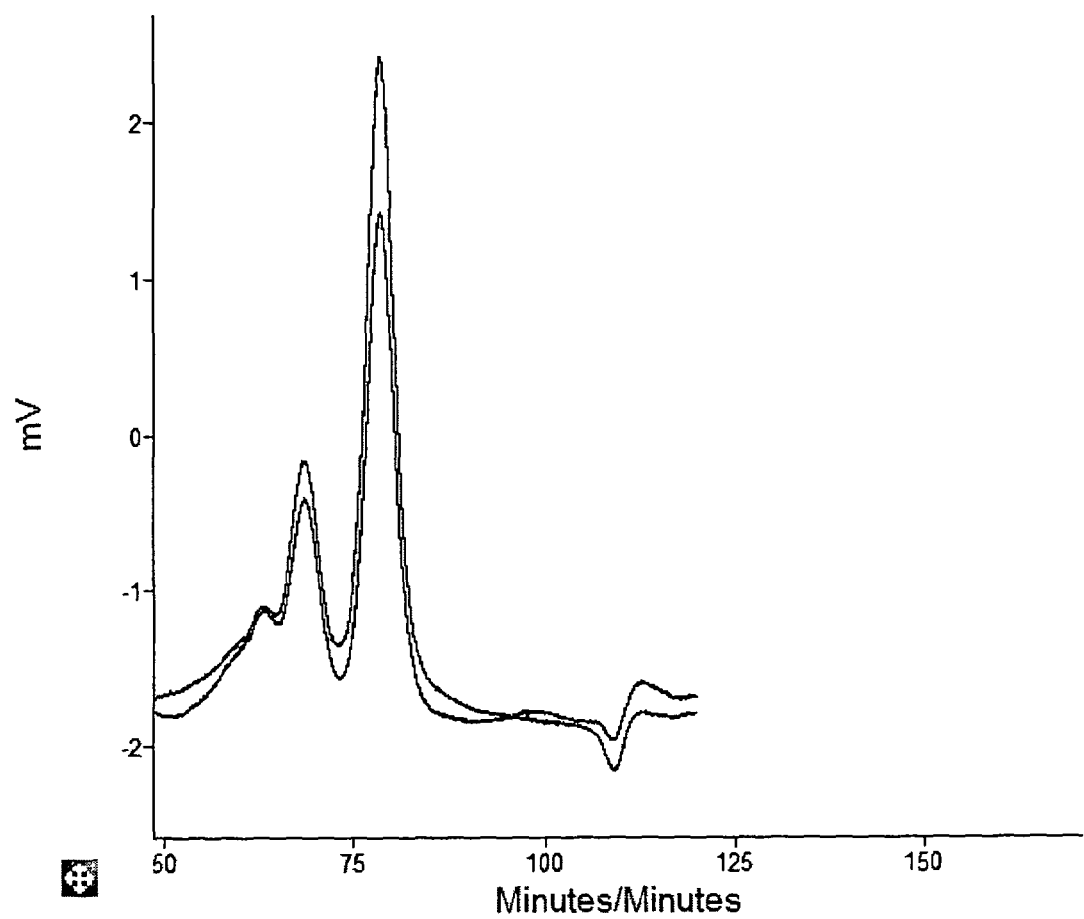
Figure 14:
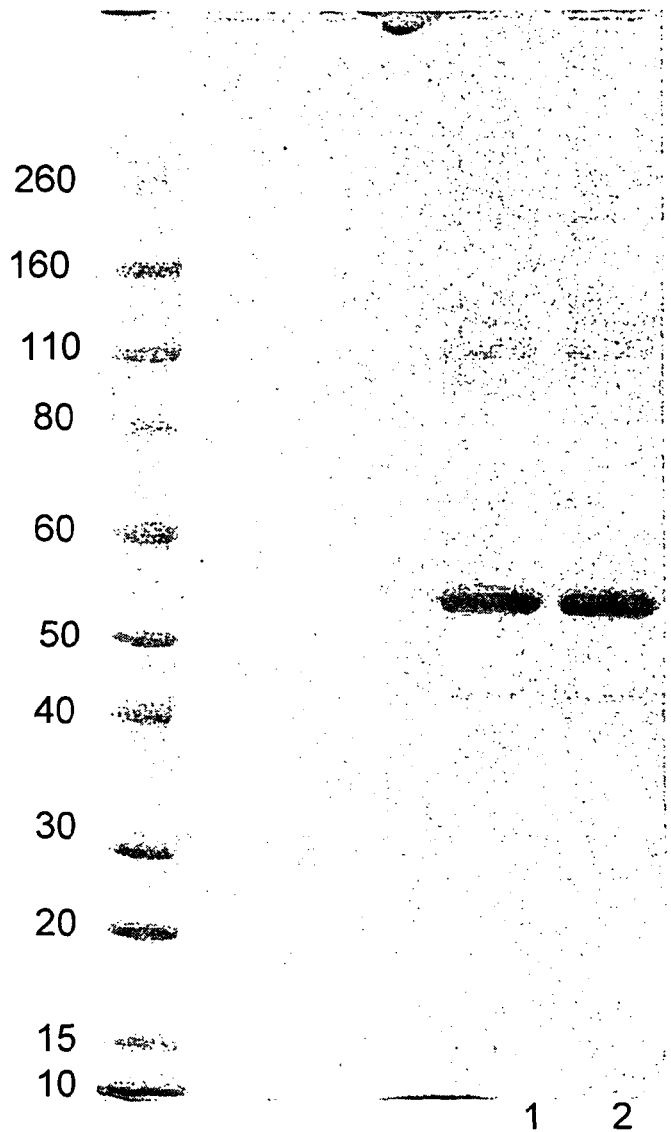
Figure 15:
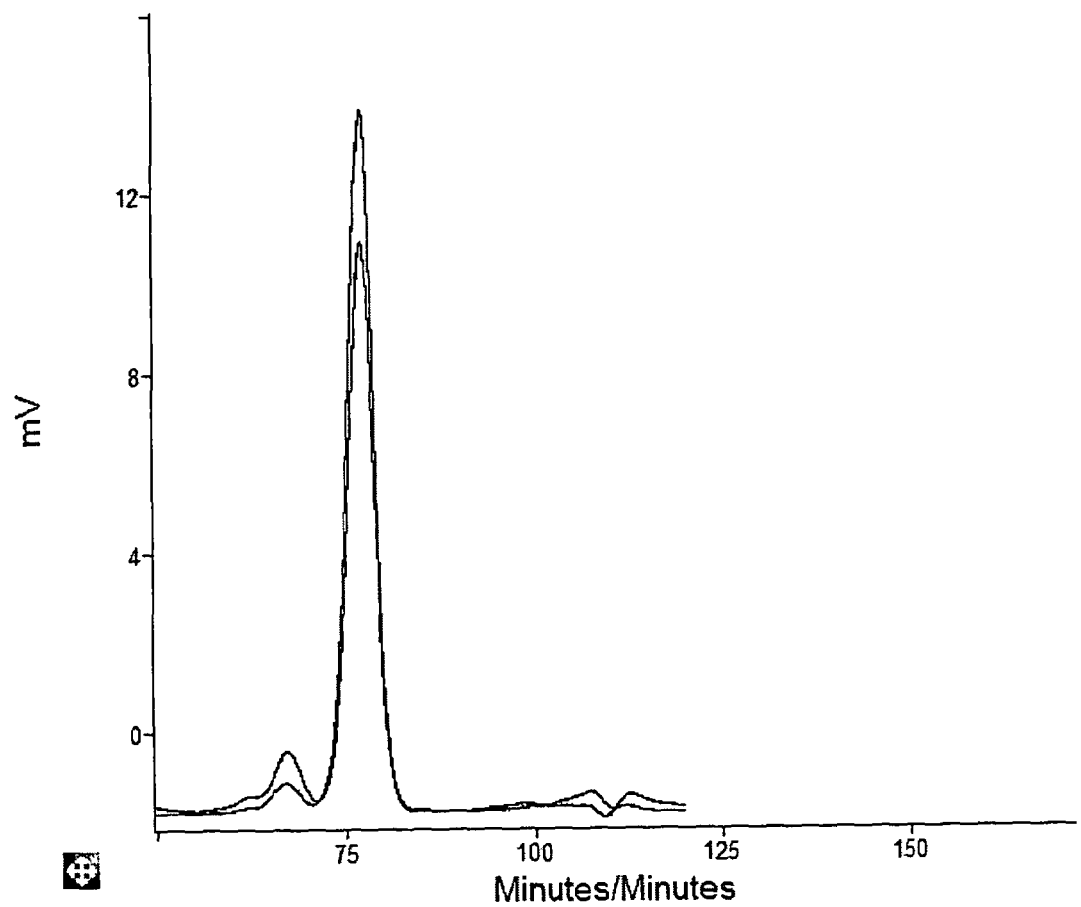
Figure 16:
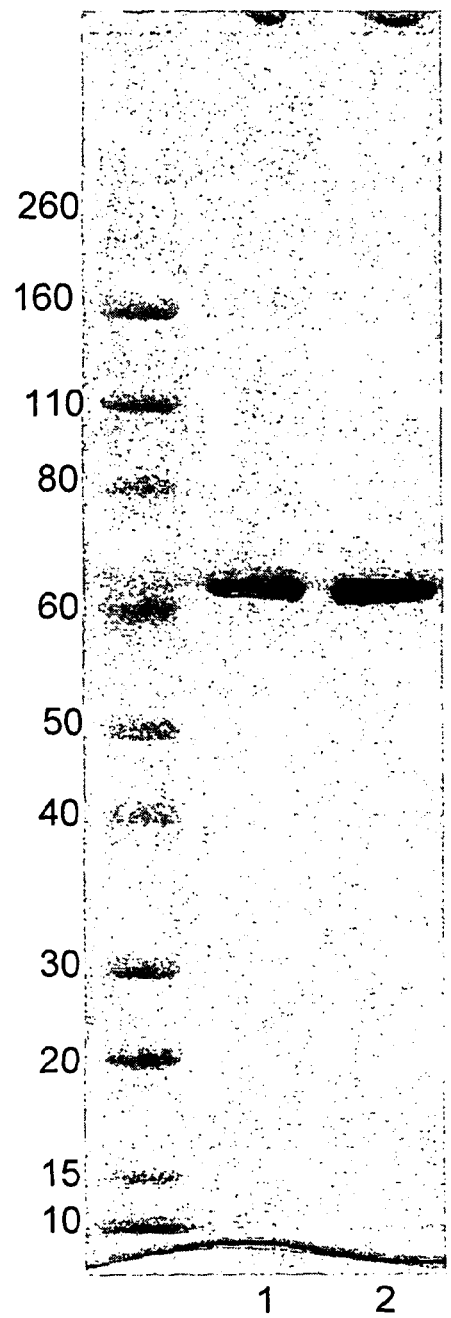
Figure 17:
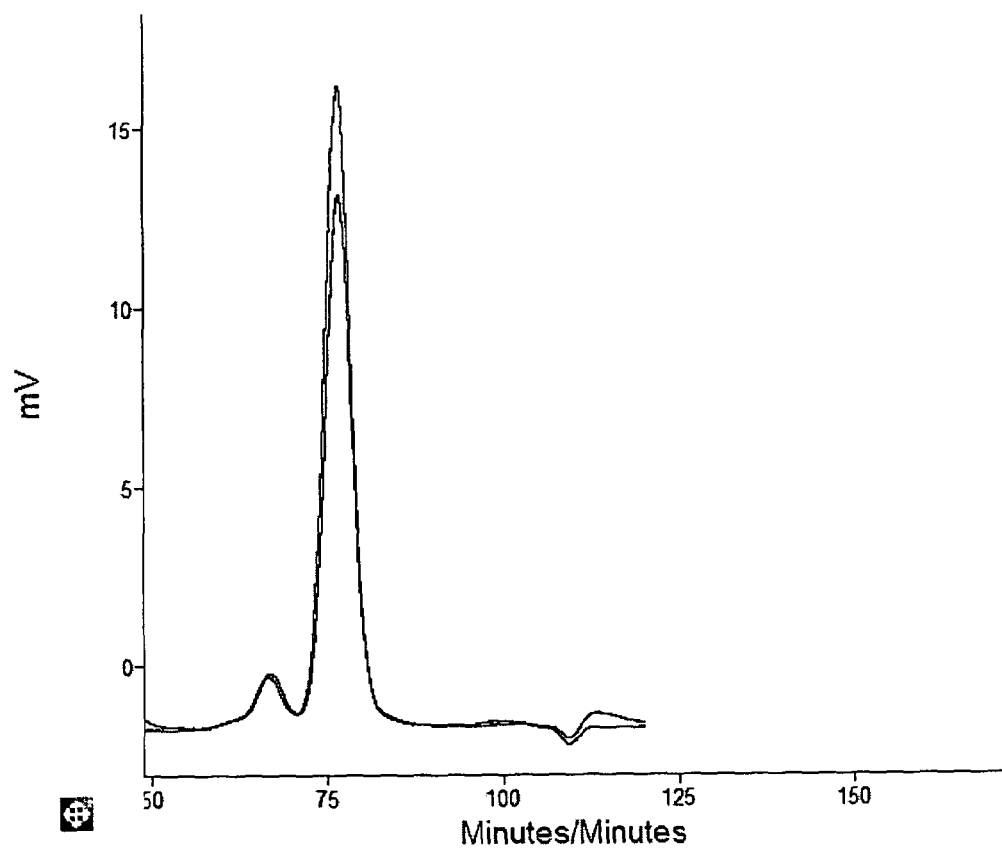
Figure 18:
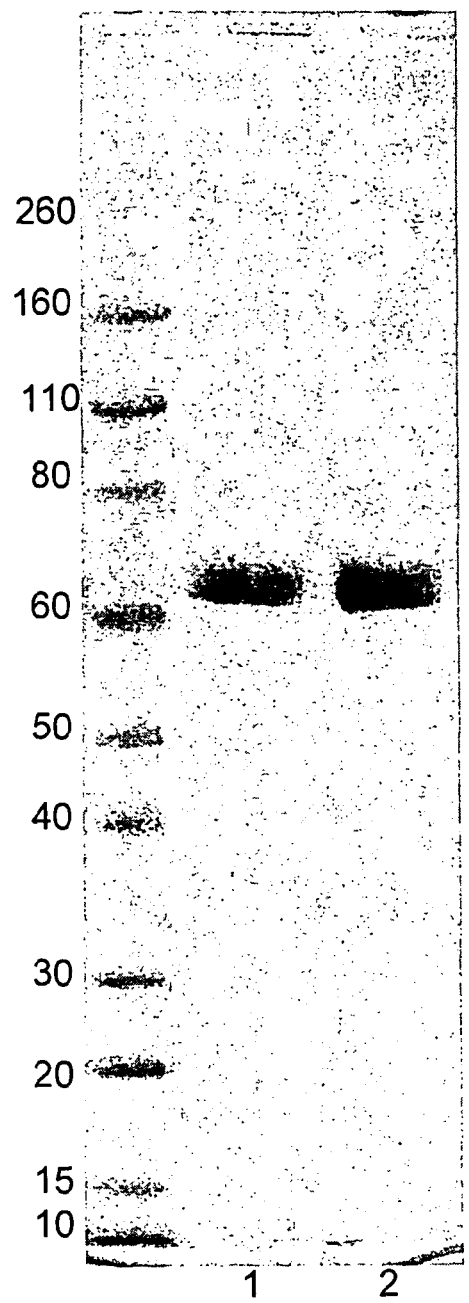
Figure 19:
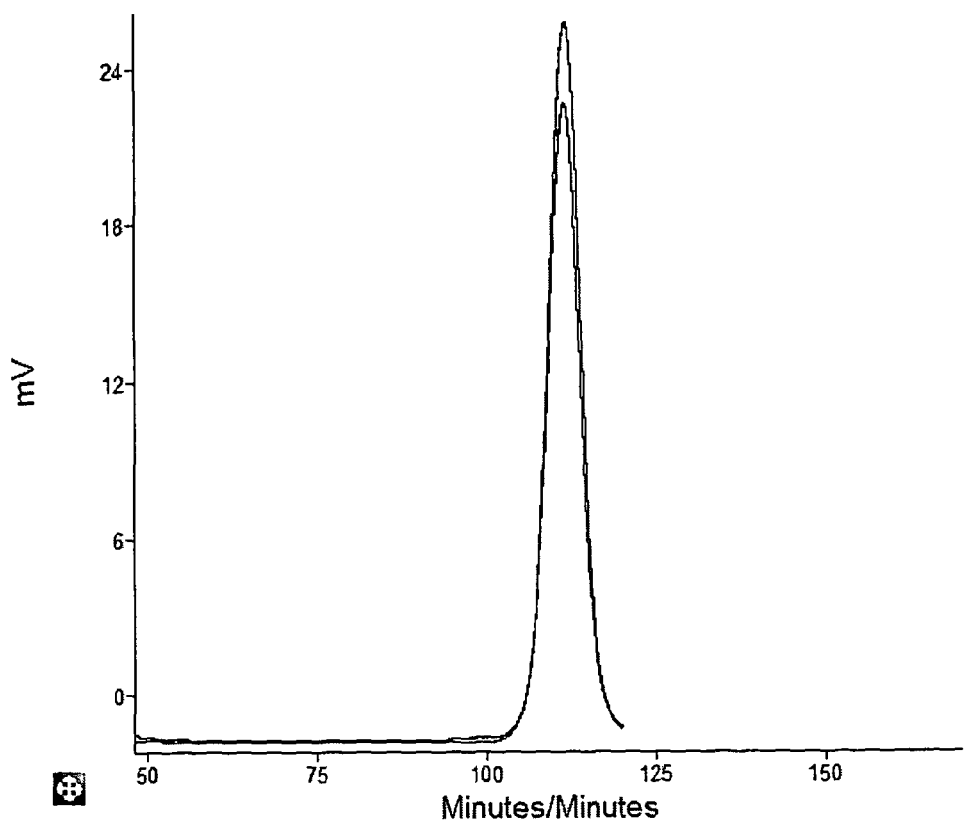
Figure 20:
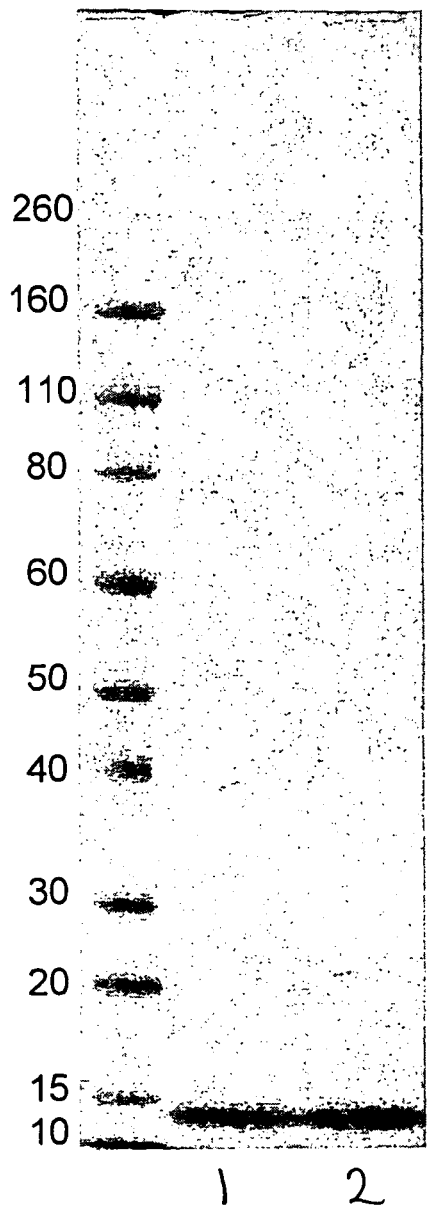
Figure 21:
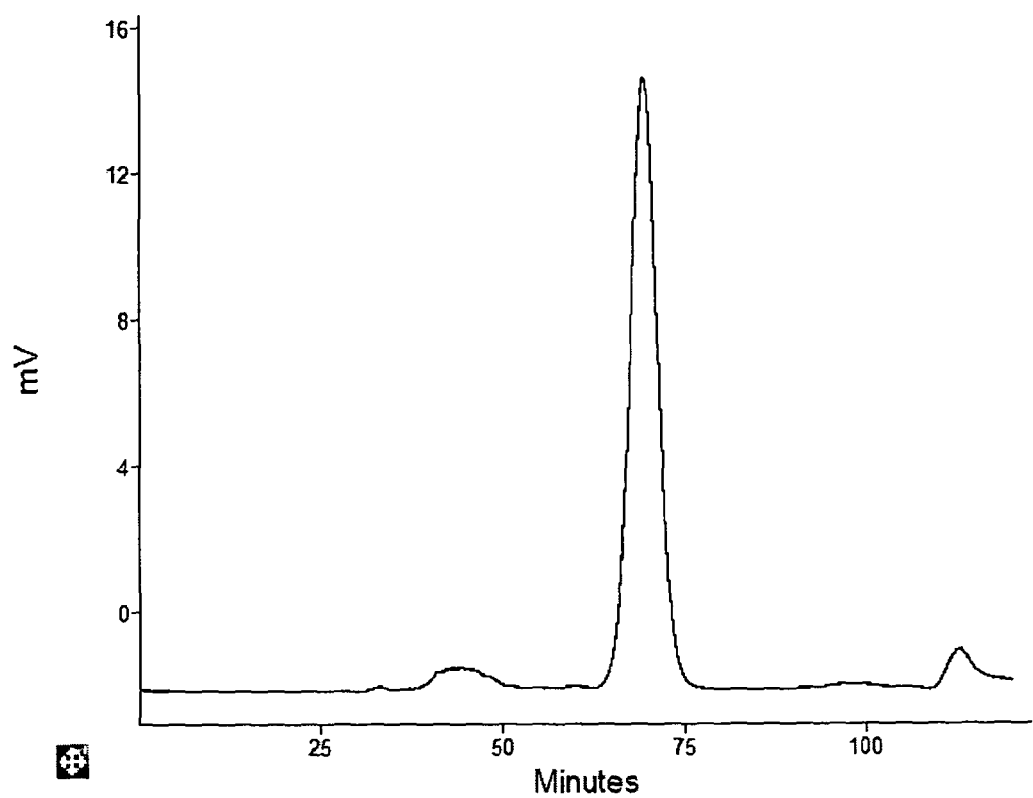
Figure 22:
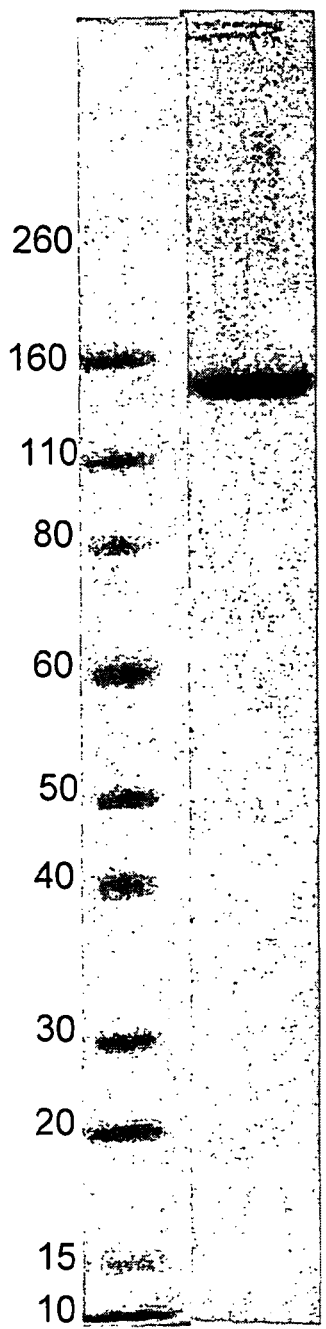
Figure 23:
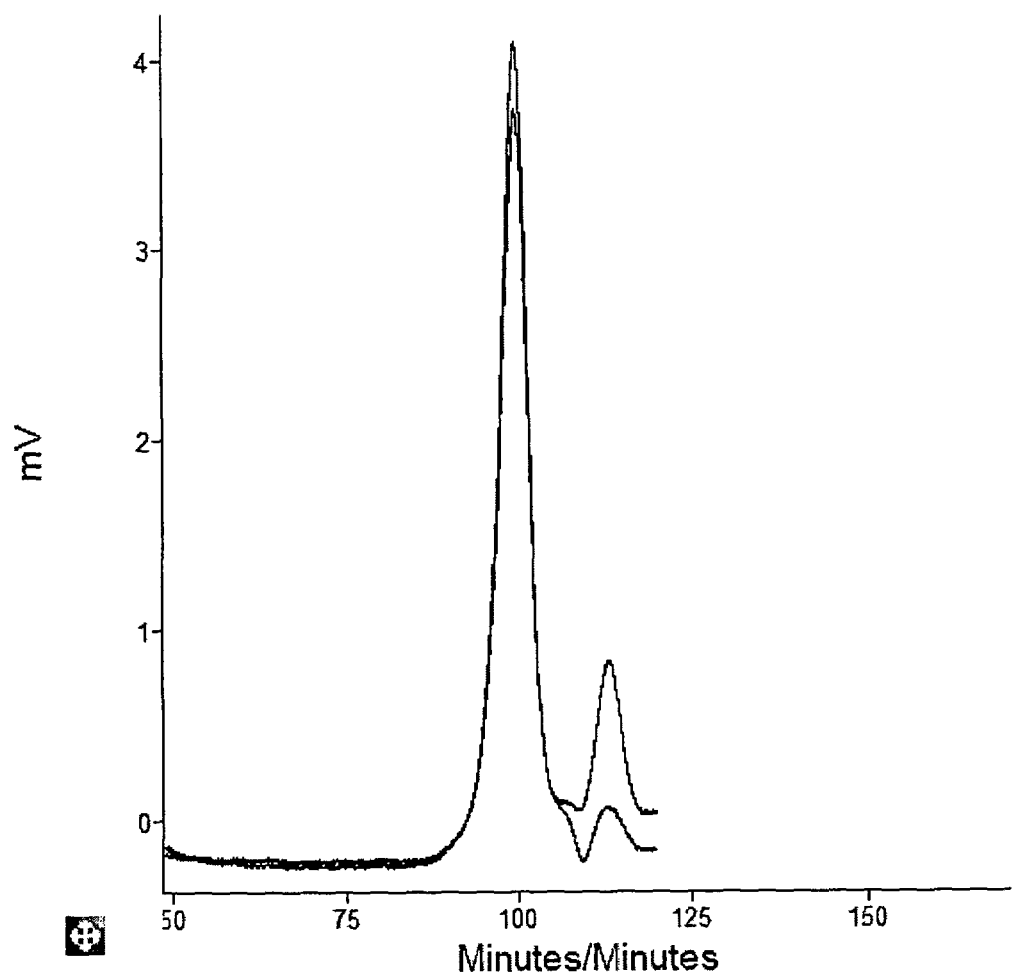
Figure 24:
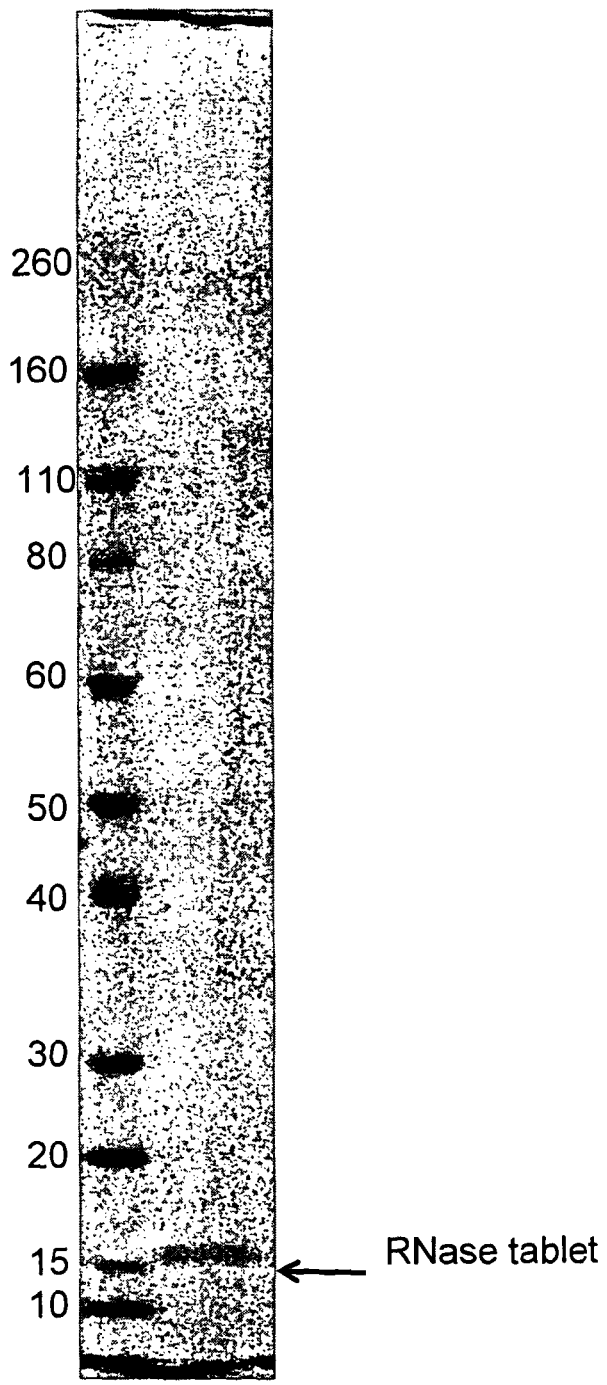
Figure 25:
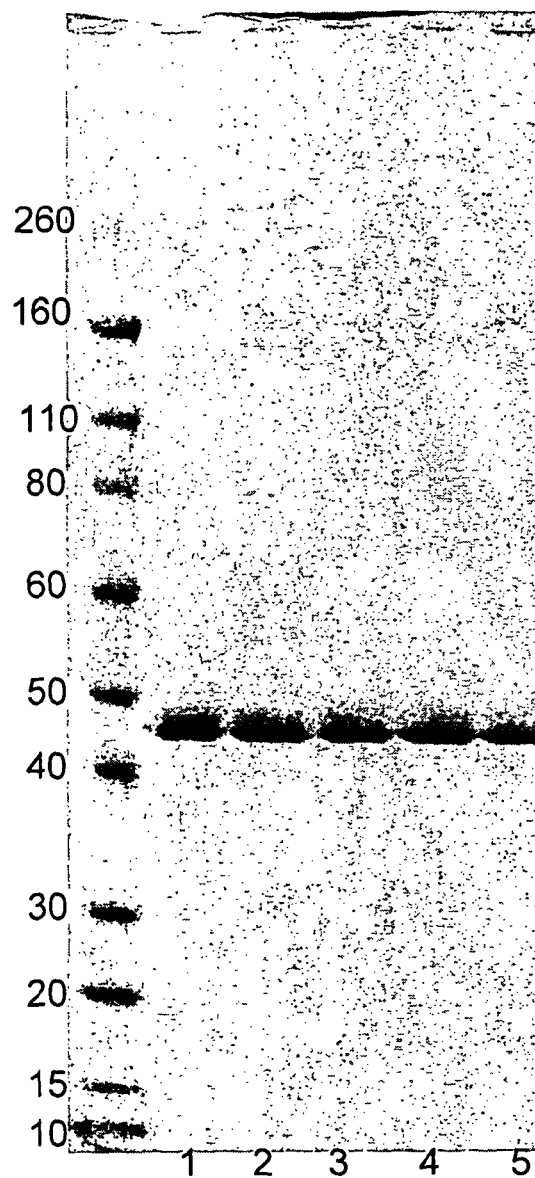
Figure 26:
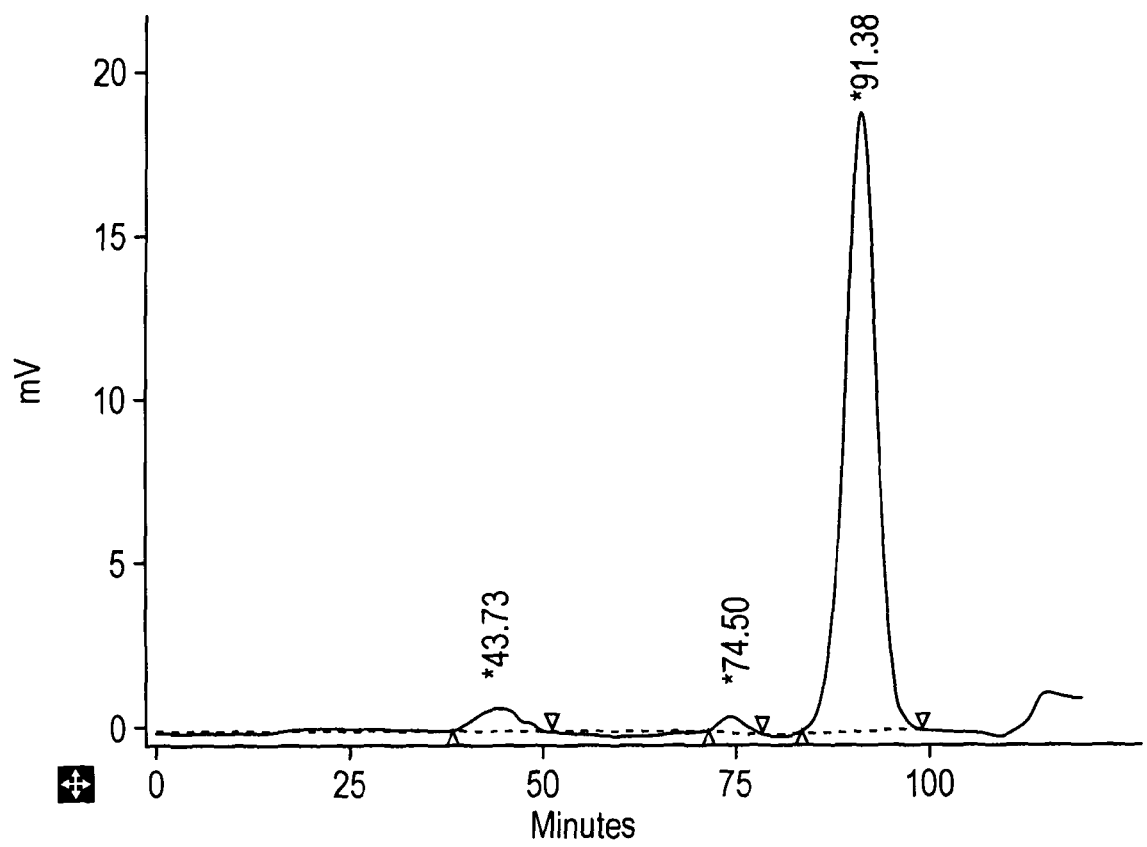

FIG. 8 shows the results of an in vivo rabbit scarring model. Five groups (n=6) as follows were examined; a) bevacizumab (Avastin®) injection, b) water sponge, c) mitomycin-C (currently gold standard treatment in clinic), d) IgG tissue tablet, e) bevacizumab tissue tablet (according to the invention). The bevacizumab tissue tablet showed a statistically significant increase in the survival of the bleb (Kaplan-Meier survival curve). This indicates the significant anti-scarring effect of the invention;

FIG. 9 shows the bleb (from the scarring model of FIGS. 7 and 8) at various time points following glaucoma filtration surgery. The black line highlights the bleb whilst the failed blebs are shown with a black spot;

FIG. 10 shows a schematic representation of a process for preparing a tablet according to the present invention;

FIG. 11 shows a molecular weight comparison (by SEC) of recombinant human insulin released from a tablet according to the invention (upper trace) with recombinant human insulin prepared in solution;

FIG. 12 shows a molecular weight comparison (by SDS-PAGE) of the anticancer agent asparaginase released from a tablet according to the invention (lane 1) with asparaginase prepared in solution (lane 2);

FIG. 13 shows a molecular weight comparison (by SEC) of recombinant human albumin released from a tablet according to the invention (lower peaking trace) with recombinant human albumin prepared in solution. Albumin is used as a model peptide to illustrate the wide applicability of the compositions of the invention;

FIG. 14 shows a molecular weight comparison (by SDS-PAGE) of recombinant human albumin released from a tablet according to the invention (lane 1) with recombinant human albumin prepared in solution (lane 2);

FIG. 15 shows a molecular weight comparison (by SEC) of holo-transferrin released from a tablet according to the invention (lower peaking trace) with holo-transferrin prepared in solution;

FIG. 16 shows a molecular weight comparison (by SDS-PAGE) of holo-transferrin released from a tablet according to the invention (lane 2) with holo-transferrin prepared in solution (lane 1);

FIG. 17 shows a molecular weight comparison (by SEC) of apo-transferrin released from a tablet according to the invention (lower peaking trace) with apo-transferrin prepared in solution;

FIG. 18 shows a molecular weight comparison (by SDS-PAGE) of apo-transferrin released from a tablet according to the invention (lane 1) with holo-transferrin prepared in solution (lane 2);

FIG. 19 shows a molecular weight comparison (by SEC) of lysozyme released from a tablet according to the invention (lower peaking trace) with lysozyme prepared in solution;

FIG. 20 shows a molecular weight comparison (by SDS-PAGE) of lysozyme released from a tablet according to the invention (lane 1) with lysozyme prepared in solution (lane 2);

FIG. 21 shows a molecular weight determination (by SEC) of trastuzumab released from a tablet according to the invention, the trastuzumab being derived from the commercial product Herceptin®;

FIG. 22 shows a molecular weight determination (by SDS-PAGE) of trastuzumab released from a tablet according to the invention, the trastuzumab being derived from the commercial product Herceptin®;

FIG. 23 shows a molecular weight comparison (by SEC) of RNase enzyme released from a tablet according to the invention (lower peaking trace) with RNase prepared in solution;

FIG. 24 shows a molecular weight determination (by SDS-PAGE) of RNase enzyme released from a tablet according to the invention;

FIG. 25 shows a molecular weight comparison (by SDS-PAGE) of the antibody fragment (Fab) ranibizumab released from a series of tablets according to the invention (lanes 2-5) with ranibizumab in solution, the ranibizumab in the tablets being derived from the commercial product Lucentis®, and the solution being the commercial product as supplied and reconstituted; and FIG. 26 shows a molecular weight determination and quantification (by SEC) of ranibizumab released from a tablet according to the invention, the ranibizumab being derived from the commercial product Lucentis®. The elution times and proportions (% of total AUC (area under the curve)) of the various eluted species are reported in the table in the Figure. The non-aggregated peptide, eluting at 91 minutes, accounts for over 93% of the peptide present.

Medicines injected into the subconjunctival space display rapid clearance from this tissue. Their local short half-life means large doses must be injected which results in dose dumping and a suboptimal drug concentration in the target tissue between each administered dose. This situation therefore requires frequent injections to maintain a therapeutically beneficial concentration of the medicine. Many active ingredients that are currently used in the clinic also have narrow therapeutic indices, so using large doses frequently is not possible. As mentioned above, WO2009/063222 shows that an implantable tablet can be used to provide slow release of an active ingredient in these circumstances. After further extensive experimentation, significant improvements have now been made in the use of a peptide, such as an antibody, to fabricate a tablet for tissue implantation (which may be referred to as a 'tissue tablet'). An antibody tissue tablet has thus been developed, which can release the antibody for a prolonged period without loss of antibody activity or evidence of antibody aggregation.

The new tissue tablets are surprising improvements over the tissue-tablets developed primarily for poorly soluble active pharmaceutical ingredients and described in WO 2009/063222. Antibodies are delicate molecules and changes in their physicochemical environment can easily result in loss of activity and aggregation. In the tablets described in WO 2009/063222, some aggregation can result. A combination of excipients and/or the use of different buffers during preparation of the formulation, have been employed to protect the antibody during tablet fabrication and use. In particular it has been found that the substitution of potassium for sodium in the excipients that are used to fabricate the tablet leads to a substantially better tissue tablet where no aggregation is observed. Antibody functionality is maintained in vitro and in vivo.

The slow-release nature of the composition of the invention can help to overcome the rapid clearance of protein based medicines from the subconjunctval space and within other regions of the eye. Therefore, the formulation can be expected to be of benefit in many diseases including corneal and posterior segment angiogenesis and glaucoma filtration surgery. In particular, the composition of the invention could provide a means to deliver protein-based medicines to posterior segments of the eye for conditions such as macular degeneration and diabetic retinopathies.

The antibody tissue tablet can be used as an implantable device in several ocular diseases. The use of monoclonal antibodies is a clinically proven approach for the treatment of ocular diseases and the tissue tablet of the invention can be a means to deliver the drug to different compartments of the eye with greater efficacy than is possible by injection (which is currently the only available method). This new and surprising method of tissue tablet delivery of a medicine can therefore replace the injection route for antibodies and other peptides. This is particularly important for the delivery of protein-based drugs including antibodies and fragments thereof to the anterior and posterior segments of the eye, cornea and conjunctival regions of the eye where there is currently significant commercial interest.

Furthermore, for many cancers, a local high concentration of protein-based medicine is desirable. Again, the composition of the invention could provide a means for achieving this.

Although the invention is exemplified herein by means of a composition comprising a particular antibody, it will be appreciated that, in principle, many protein-based medicines can be delivered locally using this approach.

EXAMPLE 1

Fabrication of Antibody Tissue Tablet

The following materials were used (amounts reported are for fabrication of one tissue tablet):
1—Avastin® (Genentech, 25 mg/mL)=50 µL equal to 1.25 mg
2—Healon GV (AMO, 14 mg/mL)=125 µL equal to 1.75 mg
3—Buffer ($K_2HPO_4$, 10 mM, pH 6.2)—adjustment of pH with phosphoric acid Sodium hyaluronate (Healon GV), 1.25 µl was placed into a spin column (Vivalspin 6 mL, with cut off membrane of 10000 Daltons) and washed with buffer, 7-8 times, using a centrifuge at 4000 rpm for 20-25 minutes at each run. The hyaluronate was then transferred to a glass vial (28 mL, 2.5 cm diameter). The volume was adjusted to 2.5 mL. Approximately 30 minutes later, the solution was vortexed to make sure it was homogeneous. Avastin® (50 µL) was diluted to 1 mL with the buffer and then added dropwise while the glass vial was on the vortex (with gentle shaking).

The vial was transferred to a freeze-drier for lyophilisation. The shelf temperature was reduced from ambient to −30° C. gradually. The shelf temperature was kept at −30° C. until the solution was completely frozen (approximately 1-2 hours). Primary drying then took place for 48-72 hours (depending on the number of samples), with the following conditions: pressure 100-110 microbar, shelf temperature −20° C., condenser temperature approximately −70° C. The process is illustrated schematically in FIG. 10.

Secondary drying was performed at 20° C. for at least 2 hours.

Afterwards, the lyophilised powder was compressed to form an implantable tablet, using a hand press, and an approximately 3 mm punch and die. A compression force of approximately 8 bars was applied for 10 seconds. After removal from the die, the tablet had a diameter of approximately 3 mm, and a thickness of approximately 0.87 mm.

EXAMPLE 2

Physicochemical Characterisation of Implantable Tissue Tablet 2.1—Peptide Release The release of bevacizumab from tablets prepared in Example 1 was determined using a flow rig designed to mimic the volume of and fluid flow through an implantation site (bleb) in the subconjunctival space (as described in WO2009/063222). The rig has a flow chamber volume of 200 µL, and a flow rate of 2 µL/minute was used. The dissolution medium was phosphate-buffered saline (PBS) at pH 7.4. Samples from the flow rig, containing the released protein, were collected and protein concentration was determined by micro BCA assay.

Figure 1:
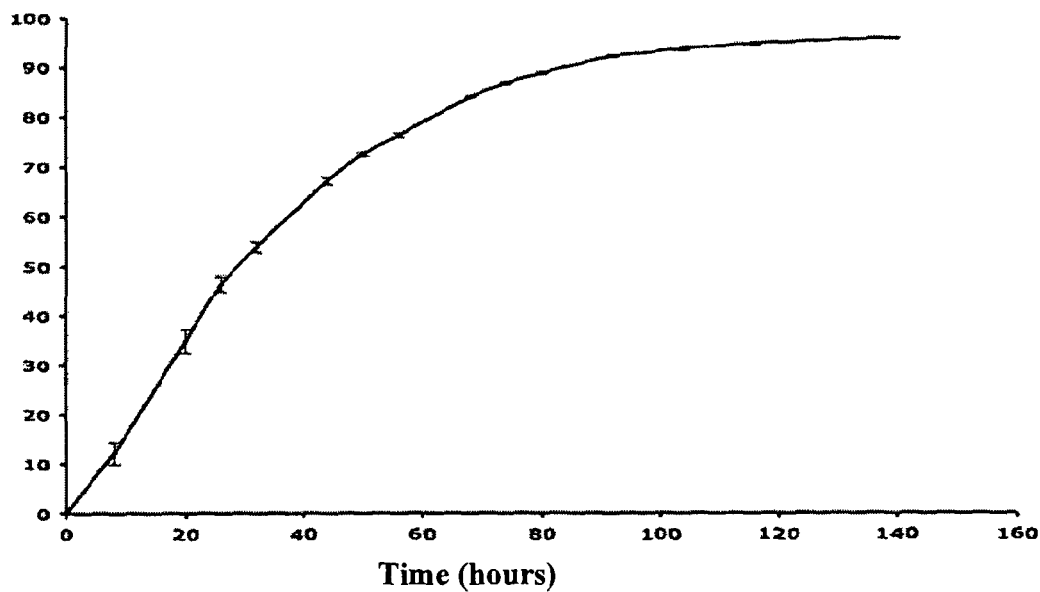

The results are shown in FIG. 1. The tissue tablet was found to release bevacizumab over a prolonged period of time—up to 150 hours (detection limit 1 µg/mL). In terms of total release, it was determined that 95.9% of the bevacizumab was released from the tablet. Near first order kinetics was observed over about the first 50 hours (FIG. 1).

Bevacizumab as Avastin® solution, was released in less than 2 hours (not shown).

2.2—Peptide Molecular Weight/Stability

Figure 2:
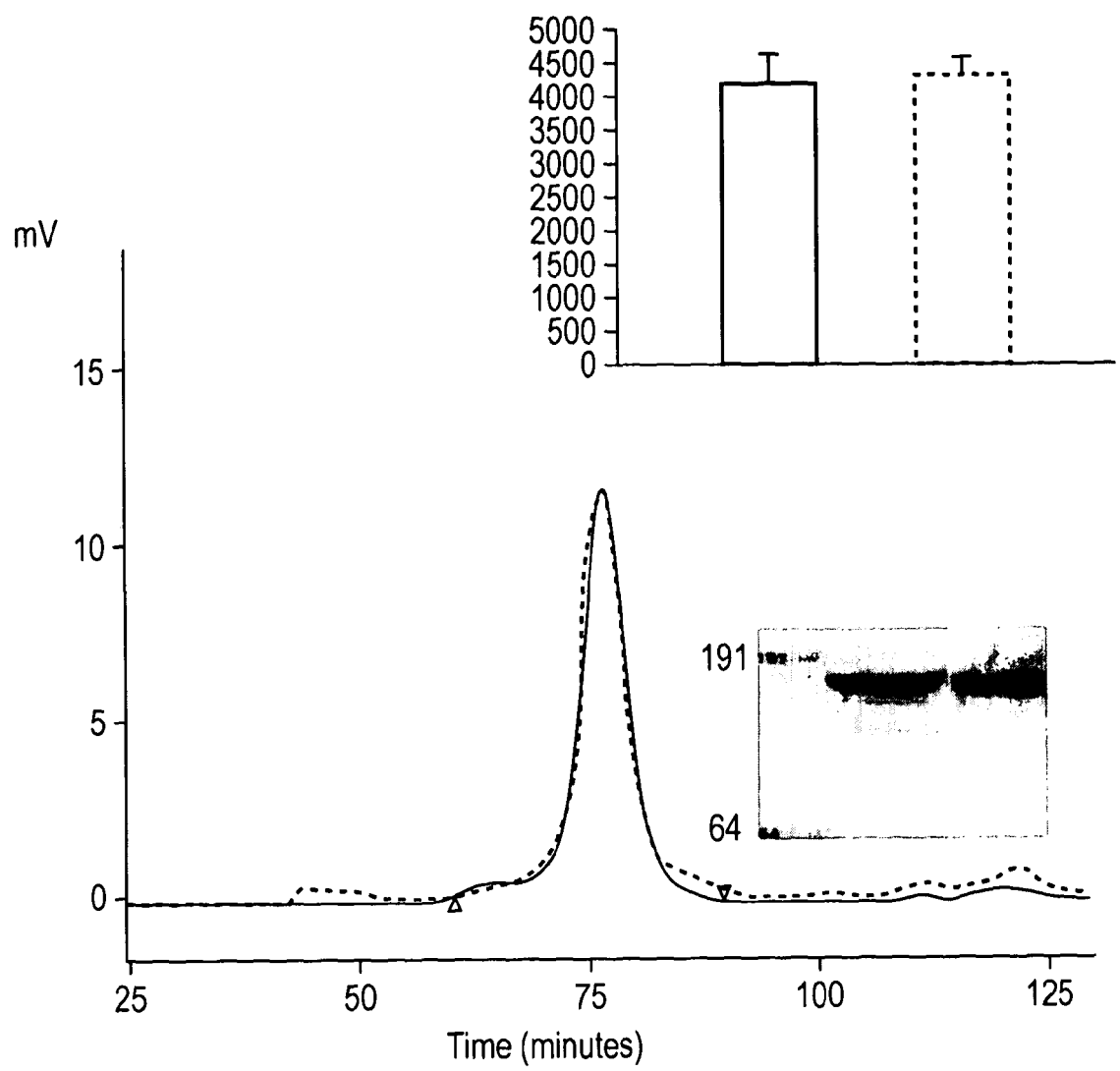

Size exclusion chromatography (SEC-HPLC) and gel electrophoresis (SDS-PAGE, bis tris 4-12% gel) were used to assess the presence of high molecular weight species and aggregates. The following SEC-HPLC condition was used; Superdex™ 200 prep grad column, $NaH_2PO_4$ (5 mM, pH 6.2) plus NaCl (150 mM) as mobile phase, UV wavelength at 280 nm, injection volume of 1.0 mL, run time as 130 minutes. There was no change in the elution time or the area under the curve by SEC-HPLC (n=3, FIG. 2). This indicates the absence of aggregation of the peptide. In addition, no high molecular weight species were observed by SDS-PAGE (FIG. 2, stained by Coomassie blue, inset).

EXAMPLE 3

Figure 3:
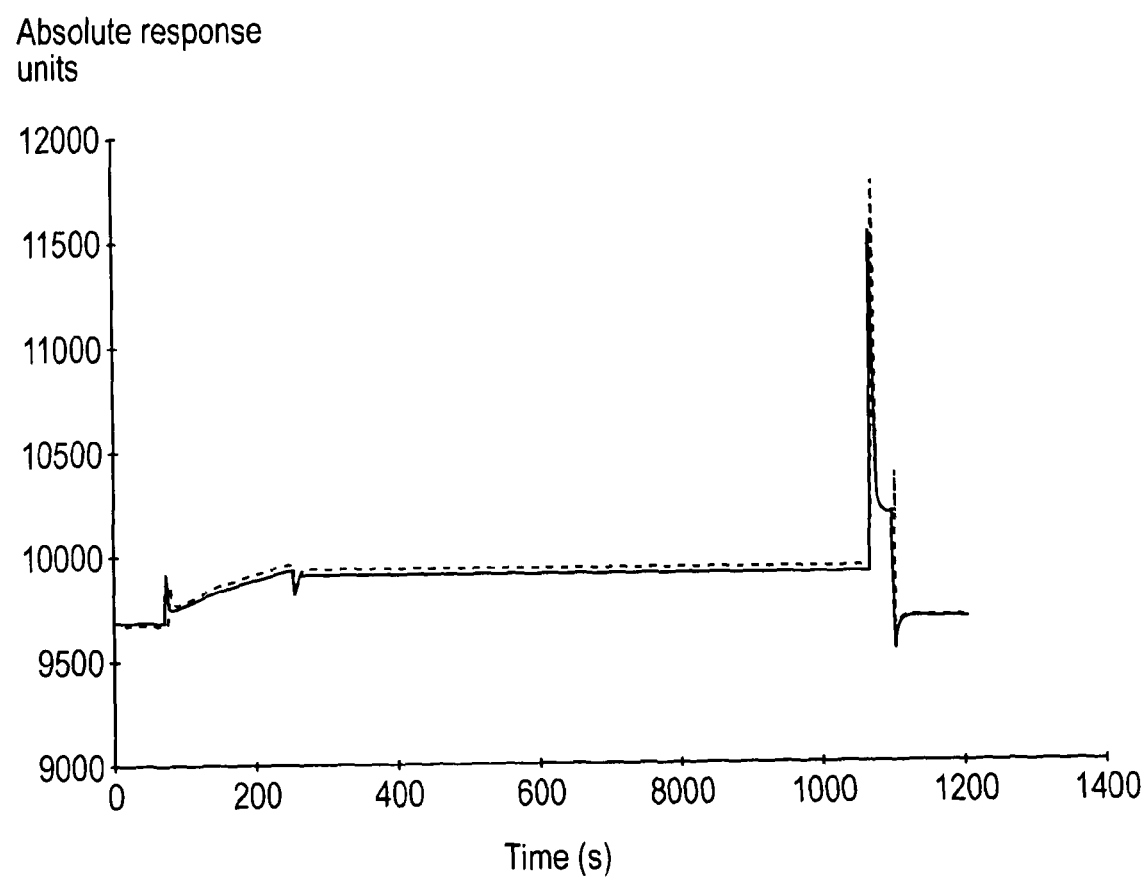

Functional and Biological Characterisation of Implantable Tissue Tablet 3.1—Antigen Binding Assessment The released antibody from the tablet was evaluated at different time points by a biosensor (surface plasmon resonance) approach. A CM5 chip has been immobilised by recombinant human VEGF 165 until a relative response of roughly 20000 was achieved. The bevacizumab tissue tablet was dissolved and examined with a similar amount of bevacizumab from the pharmaceutical formulation (Avastin, 1.25 mg). The experiment was carried out in ambient temperature using HEPES as running buffer (n=3). The dissolved antibody from tissue tablet showed similar binding to VEGF$_{165}$ as antibody released from the Avastin® formulation (FIG. 3).

3.2—Biological Activity

Figure 4:
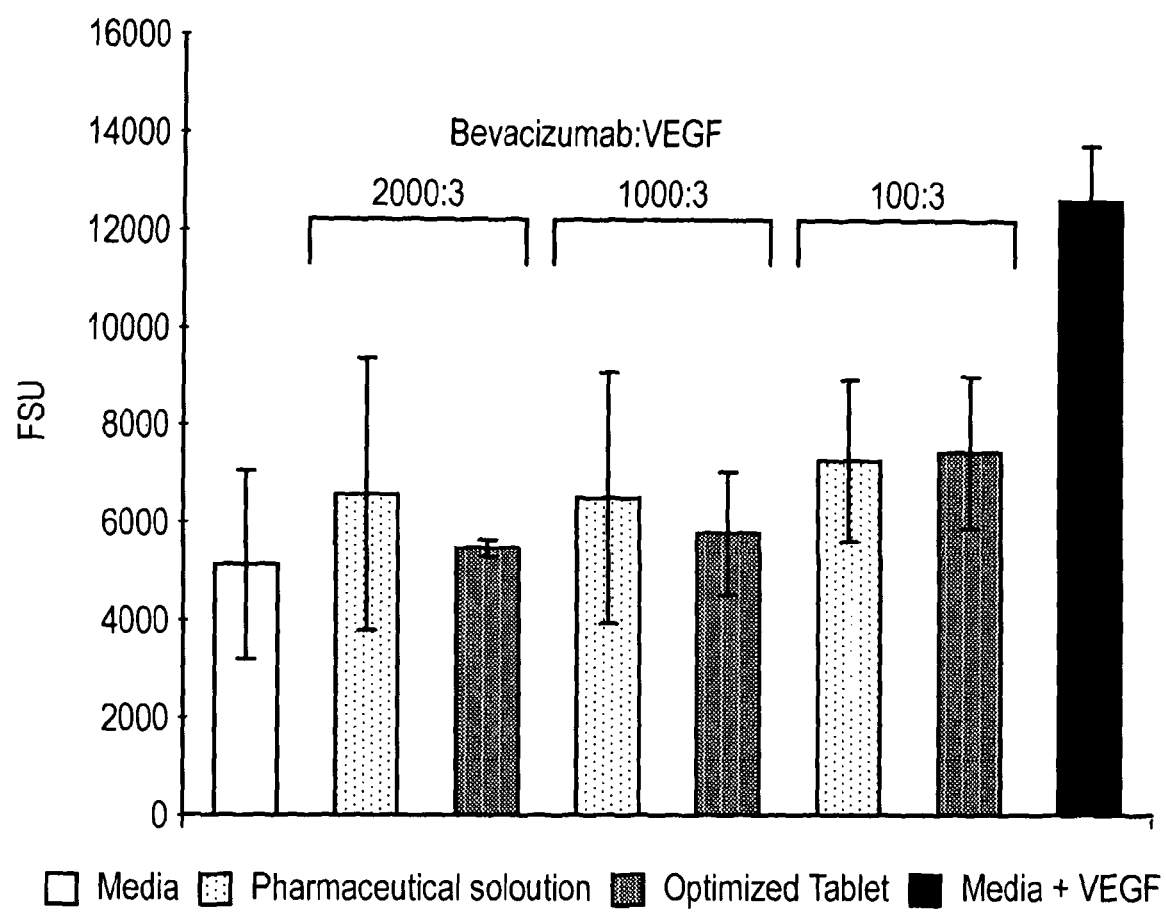
Figure 5:
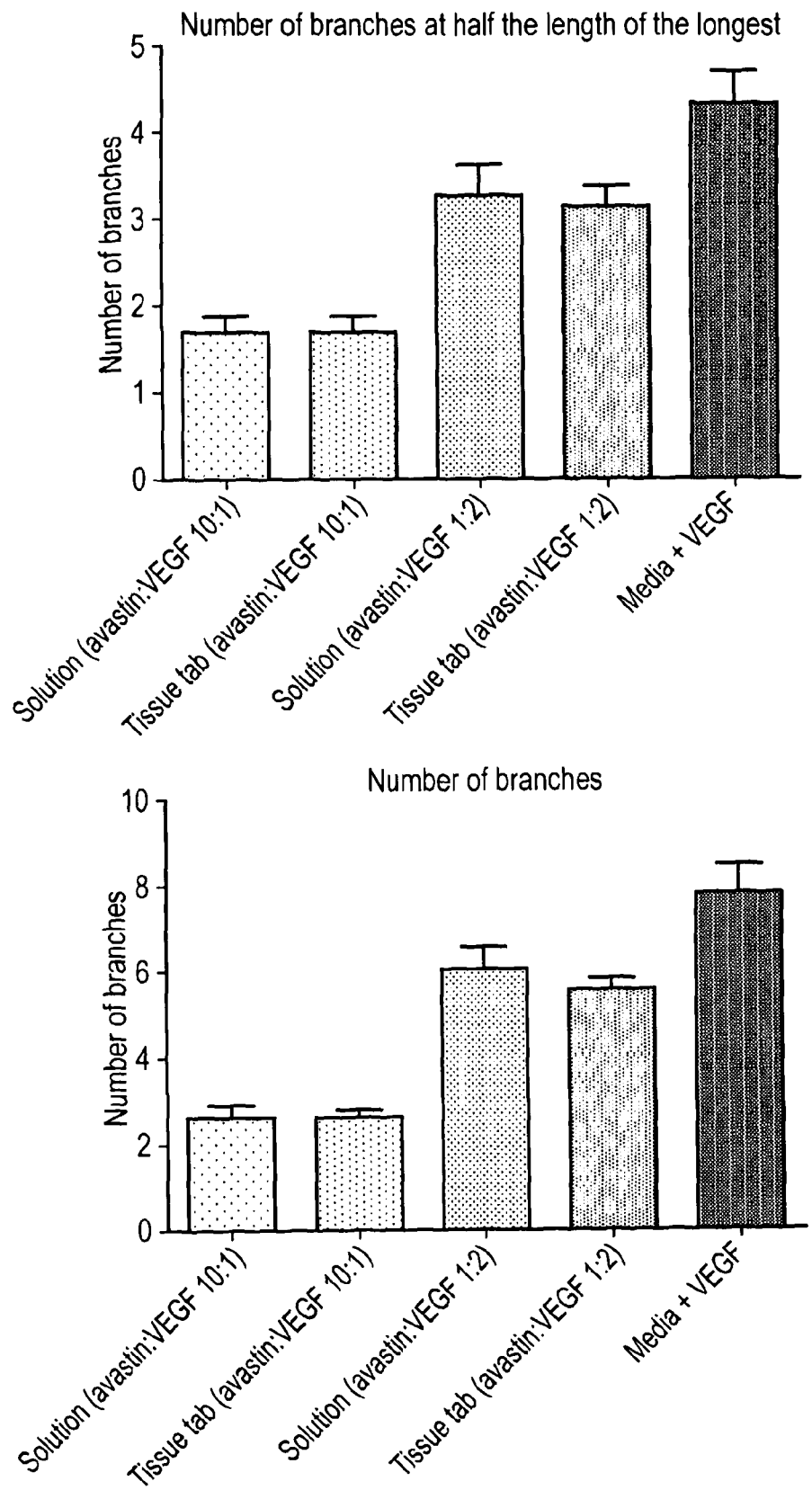

Biological studies (HUVEC cell proliferation (alamar blue assay), and co-culture angiogenesis (HUVEC and human tenon fibroblast (HTF)) assays) showed similar activity (no significant difference) between tablet and Avastin formulations (FIGS. 4 and 5). In the co culture angiogenesis assay the HUVEC were settled on the beads (roughly 400 cells per bead) and then the beads were embedded in fibrin gel. The HTF (20000 cells/gel) was added on top. The EGM2 media was used to make the conditioned media. The effect of conditioned media were examined at day 7 and 14 by measurement of 1) the length of the longest branch 2) the number of branches 3) the number of branches that reached the half length of the longest branch.

FIG. 4 shows that loss of activity can occur in tablets not according to the invention.

Figure 6:
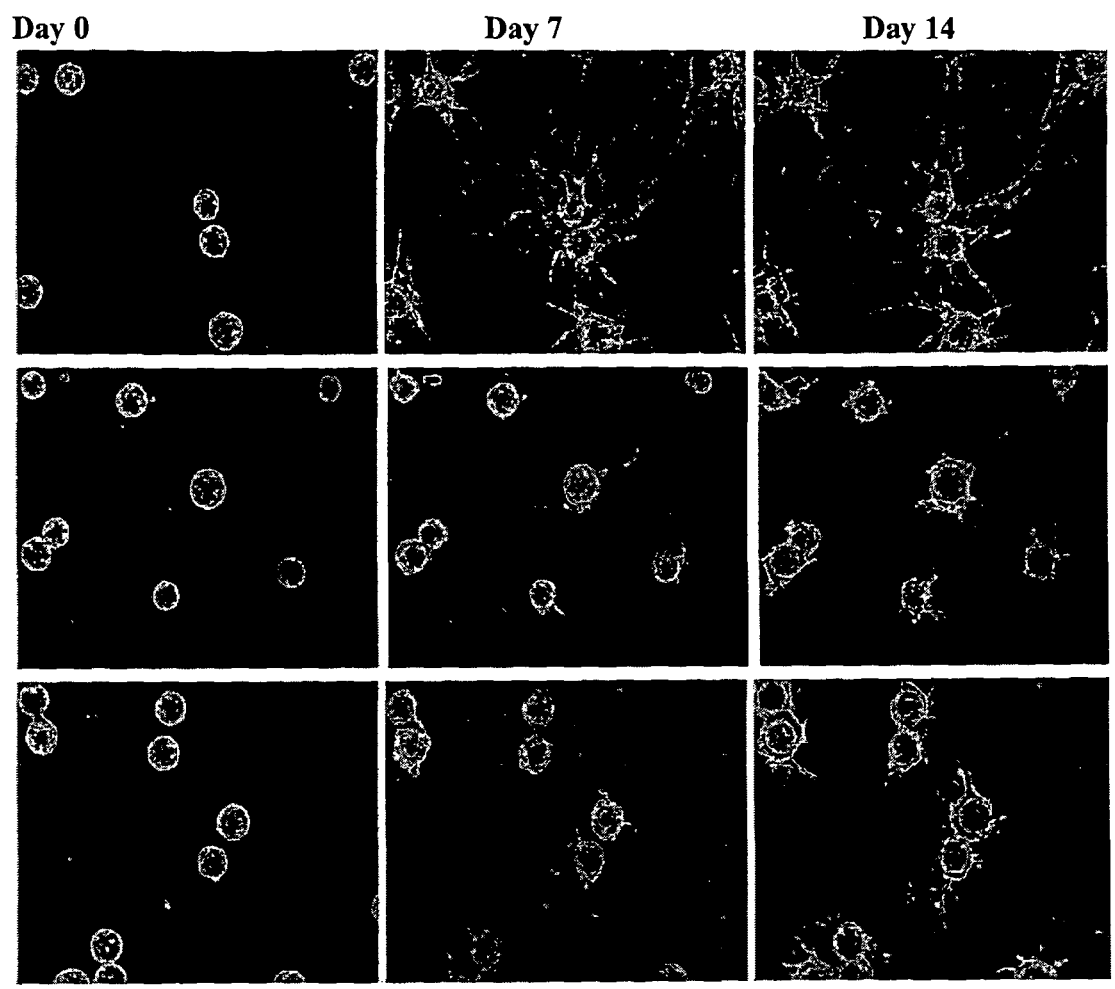
FIG. 6 shows the results of a microscopy study of VEGF-stimulated angiogenesis in the presence of media+VEGF control (top), bevacizumab from Avastin® (middle) and a bevacizumab tablet according to the invention (bottom)

In the 3D co-culture angiogenesis study (using HTF and HUVEC cells), there was no significant difference between tablet and Avastin formulations (FIG. 6). The following parameters were measured: length of the longest cell branch, the number of branches reaching half the longest length, and the total number of branches.

In conclusion, the tissue-tablet of the invention displayed prolonged release of active antibody in vitro. No significant loss of activity in vitro, nor significant aggregation, was seen.

3.3 In Vivo Evaluation

Figure 7:
FIG. 7 shows the placement of the bevacizumab tissue tablet (according to the invention) in the conjunctival pocket during the glaucoma filtration surgery in the rabbit.

A clinically validated and established model of glaucoma filtration surgery in the rabbit was employed to examine the wound healing effects of the bevacizumab tissue tablet that was fabricated as described above. Thirty rabbits were used in a randomised and blinded study. The rabbits were divided into 5 treatment groups as follows; a) bevacizumab (Avastin®) injection, b) water sponge, c) mitomycin-C (currently gold standard treatment in clinic), d) IgG tissue tablet, e) bevacizumab tissue tablet (according to the invention). An incision was made along the limbus and then a conjunctival pocket was made through blunt dissection. A sclera tunnel was made by a blade to create a fistula between the anterior chamber and the conjunctival pocket. Then a cannula was passed through to maintain the connection and was fixed to the sclera by sutures. For rabbits that received the tissue tablet, this was placed inside the conjunctival pocket (FIG. 7). Then the incision was closed. A bleb was formed following the drainage of aqueous humour to the conjunctival pocket through the fistula. Following the surgery, the bleb was clinically evaluated at various time points by one masked observer. The following criteria were used to assess the bleb functionality: a) the size of the bleb (evaluated under portable microscope), b) vascularity of the bleb, c) the depth of the anterior chamber. Images of blebs at various time points following glaucoma filtration surgery are shown in FIG. 9. The Kaplan-Meier survival curve shows the bleb survival (FIG. 8). The results indicate the significant anti-scarring effect of the tissue tablet of the invention

EXAMPLE 4

Fabrication and Characterisation of Additional Peptide Tissue Tablets

Using the same protocol as described in Example 1, tissue tablets containing the peptides listed in the following table were prepared. In each case, the specified peptide (and amount thereof) was used instead of the Avastin solution of Example 1. Hyaluronic acid and potassium ions were added as described in Example 1, with trehalose added as specified in the table. The table lists the contents of single tissue tablets in each case. Where the peptide was obtained from a commercial product, the additional components present in that product, and which were incorporated into the tissue tablet, are also specified.

| PEPTIDE | PROTEIN LOADING (mg) | TREHALOSE (mg) | Other components from the commercial pharmaceutical formulation (if applicable) |
|---|---|---|---|
| Human recombinant Insulin | 1 | 3 | |
| Human Recombinant Albumin | 1 | 3 | |
| Human Holo Transferrin | 1 | 3 | |
| Human Apo Transferrin | 1 | 3 | |
| Lysozyme | 1 | 3 | |
| Asparaginase | 1 | 3 | |
| Herceptin ® | 1.25 | 5.2 | Histidine HCl, Histidine, P-20 |
| Lucentis ® | 1 | 10 | Histidine HCl, P-20 |
| RNase | 1 | 3 | |

The characterisation of these tissue tablets is shown in FIGS. 11 to 26. In each case, the results show that the peptide active ingredient (and albumin, as a model thereof) did not undergo significant aggregation when released from the tablet. It can be seen that the tablet compositions allow the formulation of the peptides for controlled release following in vivo administration (e.g. implantation), yet without increasing the tendency of the peptide to aggregate. These results are shown to be achievable with a diverse range of peptides of differing size and physicochemical characteristics (antibodies, antibody fragments, enzymes, hormones and haematological proteins), illustrating the broad applicability of the formulation approach embodied by the invention. Note that albumin is shown in this exemplary context as a model protein (that can, however be used as an excipient in the compositions of the invention, e.g. in appropriate proportion with or instead of HA). The albumin used had the native sequence, which has a free cysteine residue—making it highly susceptible to dimerization. The results obtained with the tablet described above indicate, however, that this albumin does not aggregate in the compositions of the invention. With recombinant derivatives of albumin that do not have the free cysteine residue, stability would be expected to be even greater. The same may be expected of other peptides with reduced aggregation tendency compared to native albumin.

All documents cited above are hereby incorporated by reference herein in their entirety.

The invention claimed is:

1. A solid, compressed pharmaceutical composition comprising i) a peptide active pharmaceutical ingredient, ii) a polysaccharide excipient, and iii) an oligosaccharide excipient, wherein the polysaccharide excipient is present in the form of a potassium salt thereof.

2. A composition according to claim 1, wherein the oligosaccharide excipient is a non-reducing sugar.

3. A composition according to claim 1, wherein the oligosaccharide excipient is a disaccharide.

4. A composition according to claim 1, wherein the oligosaccharide excipient is trehalose.

5. A composition according to claim 1, wherein the polysaccharide excipient is non-sulphated.

6. A composition according to claim 1, wherein the polysaccharide excipient is a glycosaminoglycan.

7. A composition according to claim 6, wherein the polysaccharide excipient is hyaluronic acid.

8. A composition according to claim 1, wherein the composition contains one or more further, pharmaceutically acceptable excipients.

9. A composition according to claim 8, wherein the one or more further pharmaceutically acceptable excipients comprises an albumin.

10. A composition according to claim 1 wherein the composition contains potassium ions which are present as a potassium salt.

11. A composition according to claim 1, wherein the composition is sterile.

12. A composition according to claim 1, wherein the peptide active pharmaceutical ingredient, polysaccharide excipient, and oligosaccharide excipient are freeze dried, optionally in the presence of a potassium buffer salt.

13. A composition according to claim 12, wherein the peptide active pharmaceutical ingredient, polysaccharide excipient and oligosaccharide excipient are freeze dried together.

14. A composition according to claim 1, in the form of a tablet.

15. A composition according to claim 1, wherein the peptide active pharmaceutical ingredient has a molecular weight of around 0.5 kDa to around 250 kDa.

16. A composition according to claim 1, wherein the peptide active pharmaceutical ingredient is an antibody or an antigen-binding fragment thereof.

17. A composition according to claim 16, wherein the antibody is an anti-VEGF antibody.

18. A composition according to claim 1, wherein the composition is coated.

19. A composition according to claim 1, which is suitable for implantation.

20. A compressed pharmaceutical composition comprising a peptide active pharmaceutical ingredient, and potassium salt, wherein the potassium salt comprises the potassium salt of hyaluronic acid.

21. A composition according to claim 20, wherein the composition further comprises albumin.

22. A composition according to claim 1, containing one or more additional active pharmaceutical ingredients.

23. A method for the treatment or prevention of a condition selected from scarring, tumour growth and/or metastasis, vasculoproliferative conditions, conditions involving neovascularisation, vascular endothelial cell proliferation, angiogenesis, disorders of the eye selected from diabetic retinopathy, retinal vein occlusion, retinopathy of prematurity, age-related macular degeneration and choroidal neovascularisation, or for the treatment of a tumour that may be selected from brain tumour, breast tumour, kidney tumour, colorectal tumour, lung tumour, prostate tumour, head and neck tumours, stomach tumour, pancreatic tumour, skin tumour, cervical tumour, bone tumour, ovarian tumour, testicular tumour and liver tumours, the method comprising the implantation, into a suitable site of a subject in need of such treatment or prevention, of a composition according to claim 1.

24. A method for the treatment of neoplastic conditions, macular degeneration, diabetic retinopathy, or corneal angiogenesis, or for the prevention of scarring following glaucoma filtration surgery, the method comprising the implantation, into a suitable site of a subject in need of such treatment or prevention, of a composition according to claim 17.

25. A composition according to claim 17, wherein the antibody is bevacizumab.

26. A composition according to claim 10, wherein the potassium ions present as a potassium salt are present as a potassium buffer salt.

* * * * *

UNITED STATES PATENT AND TRADEMARK OFFICE
CERTIFICATE OF CORRECTION

PATENT NO.       : 9,186,414 B2                                           Page 1 of 1
APPLICATION NO.  : 13/878375
DATED            : November 17, 2015
INVENTOR(S)      : Peng T. Khaw et al.

It is certified that error appears in the above-identified patent and that said Letters Patent is hereby corrected as shown below:

In the Claims,
Claim 8, col. 13, line 8, delete "," between "further" and "pharmaceutically"
Claim 20, col. 14, line 4, insert --a-- between "and" and "potassium"

Signed and Sealed this
Fifth Day of April, 2016

Michelle K. Lee
*Director of the United States Patent and Trademark Office*